US012403463B2

(12) United States Patent
Esteves Reis et al.

(10) Patent No.: US 12,403,463 B2
(45) Date of Patent: Sep. 2, 2025

(54) SAMPLE TRANSFER DEVICE

(71) Applicant: BIOSURFIT, S.A., Azambuja (PT)

(72) Inventors: Nuno Alexandre Esteves Reis, Lisbon (PT); Tania Moura Pires De Andrade Tenreiro, Lisbon (PT)

(73) Assignee: BIOSURFIT, S.A., Azambuja (PT)

( * ) Notice: Subject to any disclaimer, the term of this patent is extended or adjusted under 35 U.S.C. 154(b) by 1065 days.

(21) Appl. No.: 17/048,900

(22) PCT Filed: Apr. 18, 2019

(86) PCT No.: PCT/EP2019/060144
§ 371 (c)(1),
(2) Date: Oct. 19, 2020

(87) PCT Pub. No.: WO2019/202102
PCT Pub. Date: Oct. 24, 2019

(65) Prior Publication Data
US 2021/0229086 A1 Jul. 29, 2021

(30) Foreign Application Priority Data
Apr. 18, 2018 (PT) ..................................... 110702 K

(51) Int. Cl.
*B01L 3/02* (2006.01)
*B01L 3/00* (2006.01)

(52) U.S. Cl.
CPC ......... *B01L 3/022* (2013.01); *B01L 3/502715* (2013.01); *B01L 3/50273* (2013.01);
(Continued)

(58) Field of Classification Search
CPC ............... B01L 3/022; B01L 3/502715; B01L 3/50273; B01L 2200/027; B01L 2200/12; B01L 2400/0409
See application file for complete search history.

(56) References Cited

U.S. PATENT DOCUMENTS

2008/0193926 A1  8/2008  Abraham-Fuchs et al.
2010/0125223 A1  5/2010  Roan
(Continued)

FOREIGN PATENT DOCUMENTS

CN   206 818 436 U     12/2017
WO   WO 2004/06770 A2   8/2004
(Continued)

OTHER PUBLICATIONS

PCT International Search Report for PCT/EP2019/060144 mailed Jul. 17, 2019, 7 pages.
(Continued)

*Primary Examiner* — Brian J. Sines
(74) *Attorney, Agent, or Firm* — Husch Blackwell

(57) ABSTRACT

A device for collecting and transferring liquid samples having a detachable sample collecting portion includes an elongated body with a liquid collecting portion disposed at one end and a handling portion disposed at the other end separated by a frangible portion. The sample collecting portion includes an inner surface configured to be wetted by the sample. After collection, the sample is transferred into a separate housing by inserting the sample collecting portion filled with sample into a confining cavity and subsequently breaking the sample transfer device along the frangible portion. The liquid sample is extracted from the collecting portion using known means to drive and control flow in fluidic devices including rotation, capillary pressure or pneumatics. The separate housing may be part of a device capable to process the liquid sample to provide for a system for handling liquid samples.

24 Claims, 27 Drawing Sheets

(52) U.S. Cl.
CPC ..... *B01L 2200/027* (2013.01); *B01L 2200/12* (2013.01); *B01L 2400/0409* (2013.01)

(56) References Cited

U.S. PATENT DOCUMENTS

2017/0023546 A1* 1/2017 Holmes ............ A61B 5/150343
2018/0021026 A1* 1/2018 Nelson .................... B01L 3/505
                                                              422/507

FOREIGN PATENT DOCUMENTS

| WO | WO 2005/115619 A1 | 12/2005 |
| WO | WO 2014/207598 A1 | 12/2014 |
| WO | WO 2017/209628 A1 | 12/2017 |

OTHER PUBLICATIONS

Written Opinion of the ISA for PCT/EP2019/060144 mailed Jul. 17, 2019, 18 pages.

\* cited by examiner

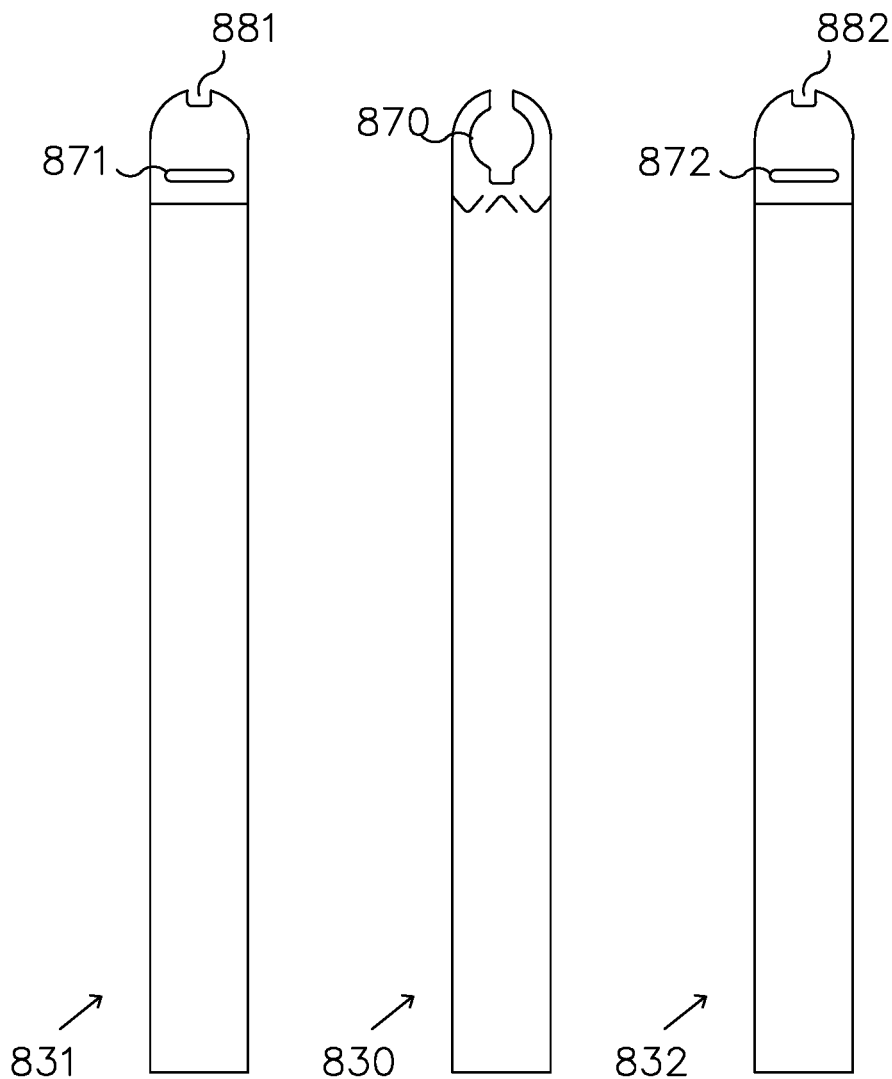

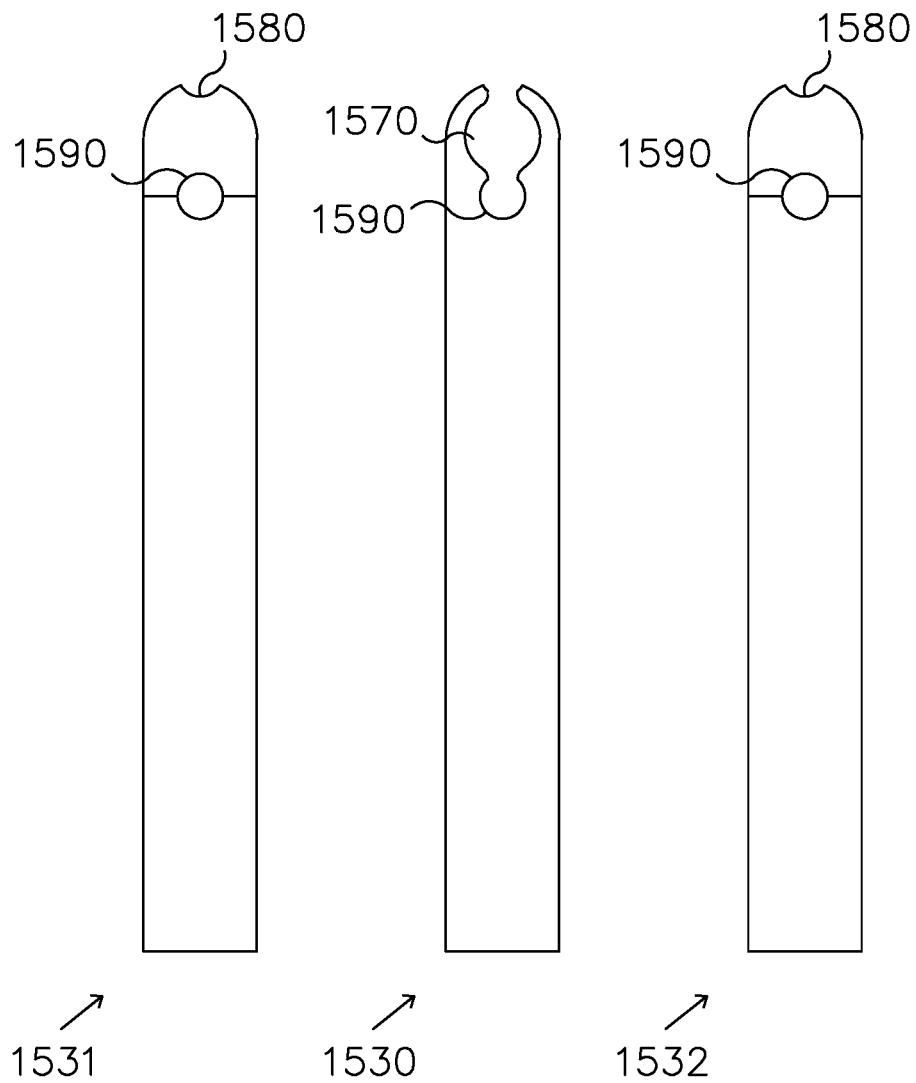

SAMPLE TRANSFER DEVICE

RELATED APPLICATIONS

The present application is a National Phase entry of PCT Application No. PCT/EP2019/060144, filed Apr. 18, 2019, which claims priority from PT Application No. 110702 K filed Apr. 18, 2018, both of these disclosures being hereby incorporated by reference in their entirety.

FIELD

The present disclosure relates to a sample transfer device comprising a detachable sample collecting portion, sets of attached sample transfer devices and methods of manufacturing the same. The present disclosure further relates to methods of using the sample transfer device to collect and transfer samples to a separate housing, systems for handling liquids employing the sample transfer device in combination with devices for processing liquid samples and methods for processing liquid samples using such systems.

BACKGROUND

Analytical devices are now widespread for a variety of applications in the laboratory, home and field use. Recently, advances in materials and manufacturing technologies prompted a generalized trend in device miniaturization and there are now a number of products in commercialization employing small foot-print analytical devices, many of which, consist of single use disposable cartridges. The latter may feature embedded reagent chemistries and detection capabilities or alternatively, designed to be integrated in a second device for assisting with diverse functions, such as sample processing or detection of specific substances.

A key aspect of usability of many analytical devices and in particular miniaturised devices is the presentation of the sample to the device. Many devices require the sample to be a liquid or a liquid preparation of the original sample. For example, products used in diagnostics such as lateral flow devices common in pregnancy test kits or blood glucose strips used in the management of diabetes employ materials and constructions which wick small drops of the intended samples exploring what is known in the art as imbibition and wetting or capillary filling. Such effects are also used in other devices, in particular those employing designed microarchitectures in which the balance between two dominant forces acting on the liquid samples, such as gravity and surface tension, trade-off as the ratio between surface area and volume of the confined sample increases. These constitute an important and rapid growing class of devices known in the art as microfluidic devices, which display intricate arrangements of fluidic passages having at least one dimension in the sub-millimeter scale. For example, some of these devices are based upon recent concepts of lab on a chip, lab on a card, lab on a strip or lab on a disc, which integrate a variety of functions for processing and analyzing samples and are constructed in small dimensions, or at least, thin geometries.

The widespread use of miniaturized, or otherwise thin, devices in a variety of settings present significant challenges in sample handling and management. First, the sample volumes are relatively small (typically microliters) and thus require specialized devices such as micro-pipettes or capillary collection tubes. These are common in laboratories but are less usual at home or field settings. Even with such devices provided by manufacturers, transferring small samples, through small apertures in miniaturized devices, is prone to operator error often resulting in compromised results or poor user experience.

Inspired by the examples of lateral flow technology or blood glucose strips, some disposable cartridges are provided with wicking or capillary filling capabilities to allow for direct sample collection using the analytical device by touching a surface of the liquid sample. Despite being simple in concept, this choice requires the device to contact potentially contaminated or hazardous samples and cleaning excess sample is not always possible as this can also remove or contaminate the intended liquid sample volume. As a consequence, additional measures or device complexity are required in order to contain the hazard of devices contaminated with samples at the external surface. In addition, this choice is also very limiting with respect to collecting samples from narrow containers such as vials (for example containing quality control solutions to ascertain analytical device condition) or test tubes from earlier collected samples, in which cases, a transfer device is still needed. Transfer devices used for these purposes are also potentially contaminated and need to be discarded according to the applicable Health and Safety Regulations.

SUMMARY

Aspects of the disclosure are set out in the independent claims. Further, optional features of embodiments are set out in the dependent claims.

In overview, liquid sample transfer devices featuring detachable sample collecting portions, sets of attached sample transfer devices and methods of manufacturing the same are disclosed. Also disclosed are methods of using sample transfer devices to collect and transfer samples to separate housings, systems for handling liquids employing the sample transfer devices and methods for processing liquid samples using such systems.

In one aspect, a sample transfer device for receiving and holding a liquid sample is disclosed. The device comprises an elongate body having a first end opposed to a second end in the elongate direction, a handling portion disposed at the first end and arranged to provide for gripping and handling means and a sample collecting portion disposed at the second end and arranged to provide for means to receive a volume of a liquid sample. The device further comprises a frangible portion disposed between the handling portion and the sample collecting portion, wherein the frangible portion is configured to enable complete separation of the sample collecting portion from the sample transfer device.

The elongate body allows for collecting samples with a comfortable distance between the handling portion and the liquid sample. This prevents contaminations, from or to, the liquid sample, and exposure of the user to potentially hazardous substances present in the sample. Samples to be handled with the sample transfer device may be of diverse types and origins such as, for example, biological samples, environmental samples, food samples, or cosmetic samples.

The frangible portion typically comprises a reduction of the device resisting cross section configured to resist mechanical loading during sample collection and handling when the device is mostly unconstrained, such as for example bending of the elongate body. The main purpose of the resisting cross section reduction is to promote rupture or fracture when the device is constrained and mechanically loaded, as it favours localised deformation at the frangible portion. The reduction in device resisting cross section may be notch or a through cut to yield separate cross sections of smaller dimensions. The mechanical deformation along the frangible portion leading to separation of the sample collecting portion from the device may be achieved, for example, by bending, tearing or twisting the handling portion relative to the sample collecting portion. Preferably, the sample collecting portion is confined or supported on a separate surface or surfaces prior to separation. In other words, the sample collecting portion is secured against movement in at least one direction, when the handling portion is moved partially or totally in that same direction.

The frangible portions according to the present disclosure may comprise one or more perforations through the thickness of the elongate body. In some embodiments, the perforation extends in at least two directions perpendicular to the thickness direction. In other embodiments, the frangible portion comprises at least two perforations through the thickness of the device. The perforations may have different shapes or the same shape disposed in different orientations. In some other cases, all perforations extend in at least two directions perpendicular to the thickness direction.

The sample collecting portion according to the present disclosure, typically comprises a surface configured to be wetted by the liquid sample. For example, the surface may be hydrophilic or lipophilic in nature, i.e., wetted by water as opposed to be wetted by oils and fats, or vice versa. In other embodiments, the surface is defined as the internal structure of porous media pads such as for example filter pads, membrane pads and woven or non-woven fabric pads. In these embodiments samples are absorbed by the porous material touching the liquid surface, and the overall pad dimensions and internal pore structure determine the maximum volume of sample collected.

In some embodiments, the sample collecting portion comprises at least one cavity wherein the at least one cavity comprises at least one aperture serving as inlet port for the liquid sample and at least one other aperture to act as vent as the sample fills the cavity. In preferred embodiments, the cavity is defined between two opposite and substantially parallel inner surfaces, wherein one or both inner surfaces are configured to be wetted by the liquid sample. In this manner, the samples are drawn into the cavity of the sample collecting portion simply touching the liquid surface with the aperture serving as liquid inlet port. The cavity geometry may also be defined as a perforation through a spacer layer positioned between a first and second outer layers, each of which define an inner surface of the cavity. The maximum sample volume collected is determined by the cavity geometry and dimensions and the position of the apertures serving as inlet and vent. In some embodiments, the inlet port and air vent are substantially coincident with a perforation through the first or second outer layers. In some other embodiments, the perforation or perforations through the first and second outer layers are perfectly aligned.

In some embodiments, the sample collecting portion may comprise more than one surface configured to be wetted by the liquid sample to collect more than one volume of a liquid sample or samples. In this manner, it is possible to use the same device to collect and transfer more than one volume of a liquid sample or samples. For example, the sample collecting portion may be arranged with two separate liquid absorbent pads or two separate cavities.

In another aspect, sets of attached sample transfer devices are disclosed. The set comprises a plurality of sample transfer devices connected by frangible connections between adjacent pairs. The frangible connections are broken to separate individual sample transfer devices from the set, in order to be used. The frangible connections between sample transfer devices are preferably disposed in the handling portion as to avoid premature damage or weakening of the sample transfer device frangible portion.

In another aspect, a method of manufacturing a plurality of sample transfer is provided. The method comprises receiving material as sheets, structuring the sheets to provide perforations or resizing width, aligning and bonding the different sheets, and finally cutting though the layered construction to yield either separate sample transfer devices or sets of attached sample transfer devices with frangible connections between adjacent pairs. The sheets of different materials may be provided as discrete units or in roll format.

In another aspect, methods of using a sample transfer device for collecting and transferring liquid samples to a separate housing are disclosed. These involve contacting a liquid with the sample transfer device to collect the sample by wetting at least one surface of the sample collecting portion, inserting the sample collecting portion of the sample transfer device into the housing to confine the sample collecting portion against movement in at least one direction, breaking the sample transfer device along the frangible portion to leave the sample collecting portion filled with sample inside the housing, and subsequently driving flow of the liquid sample out of the sample collecting portion. The method may include an additional cleaning step after collecting the sample and before inserting the sample collecting portion of the sample transfer device into the confining housing. The flow of the liquid sample out of the sample collecting portion may be driven by a differential in pressure generated using a variety of means such as for example, gas pressure, capillary pressure or centrifugal pressure.

In one other aspect, systems for handling liquids using the sample transfer device are disclosed. The systems comprise the sample transfer device according to the present disclosure in addition to a device for processing liquid samples and means to drive and control liquid flow inside the device for processing liquid samples. The latter is provided with at least one aperture in communication with at least one receiving cavity, wherein the at least one receiving cavity is configured to receive and retain the sample collecting portion of the sample transfer device. The receiving cavity in the device for processing liquid samples is arranged to provide for a tight (or interference) fit in at least one direction to secure the sample collecting portion during separation of the handling portion. When the sample collecting portion of the sample transfer device is inserted and secured in position, the frangible portion may be preferentially positioned near or at an edge of the device for processing samples aperture, as to further facilitate rupture along the frangible portion.

In some embodiments, it may be advantageous to arrange the receiving cavity of the device for processing liquid samples as an undercut extending laterally from the aperture. In other words, the cavity is disposed substantially parallel and near to an external surface of the device for processing liquid samples. This arrangement is particularly useful for devices for processing liquid samples configured in thin formats such as for example, lab on chip, lab on a disc or lab on card devices, wherein the device thickness is typically much smaller than other device dimensions, and the allowed penetration along thickness is minimal. In these cases, the sample transfer device must exhibit flexibility as it needs to bend in order to slide in the laterally disposed undercut and the frangible portion configured to resist the bending stresses without inducing any significant deformation leading to premature detachment of the sample collecting portion.

For simplicity of use, it may be advantageous to provide an aperture in the device for processing liquid samples larger than the sample collecting portion cross section, and for the cavity to be arranged to continuously narrow with smooth surfaces to self-guide the sample collecting portion into a fit position. Alternatively, the sample collecting portion may be narrower at the tip which first enters the device for processing samples, and enlarge to a cross section tight fitting the cavity in at least one direction as it reached its intended position inside the device for processing samples.

In another aspect, methods for collecting and processing a liquid sample using systems for handling liquid samples are disclosed. These involve collecting a liquid sample using the sample transfer device by wetting at least one inner surface of the sample collecting portion with the liquid sample, inserting the sample collecting portion of the sample transfer device into the device for processing liquid samples, breaking the sample transfer device along the frangible portion to leave the sample collecting portion filled with the liquid sample inside the device for processing liquid samples; and generating a differential pressure to drive flow of the liquid sample out of the sample collecting portion and into the device for processing liquid samples; and controlling the differential pressure to drive liquid flow inside the device for processing liquid samples to process the liquid sample.

BRIEF DESCRIPTION OF THE FIGURES

Specific embodiments are now described to illustrate aspects of the disclosure and by way of example with reference to the accompanying drawings, in which:

FIG. 8A to FIG. 8F illustrate a specific configuration of the sample transfer device;

FIGS. 15A to 15E illustrate a further specific configuration of a sample transfer device.

DETAILED DESCRIPTION

The disclosure provides a sample transfer device comprising a detachable sample collecting portion. Methods of using the sample transfer device to collect and transfer samples to a separate housing, systems for handling liquids employing the sample transfer device in combination with devices for processing liquid samples and methods for processing liquid samples using such systems, are also disclosed.

Figure 1:
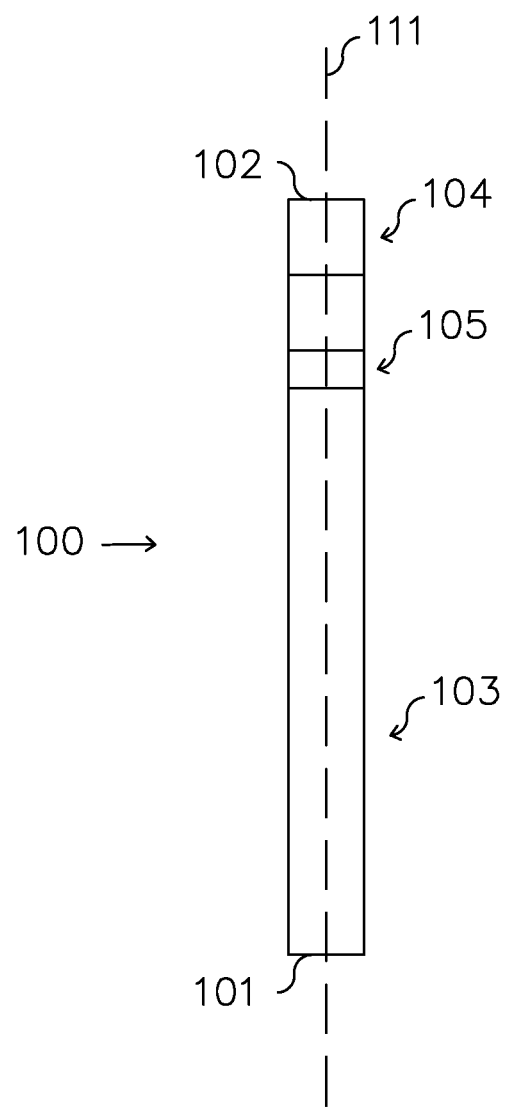
FIG. 1 illustrates a sample transfer device.
Figure 2A:
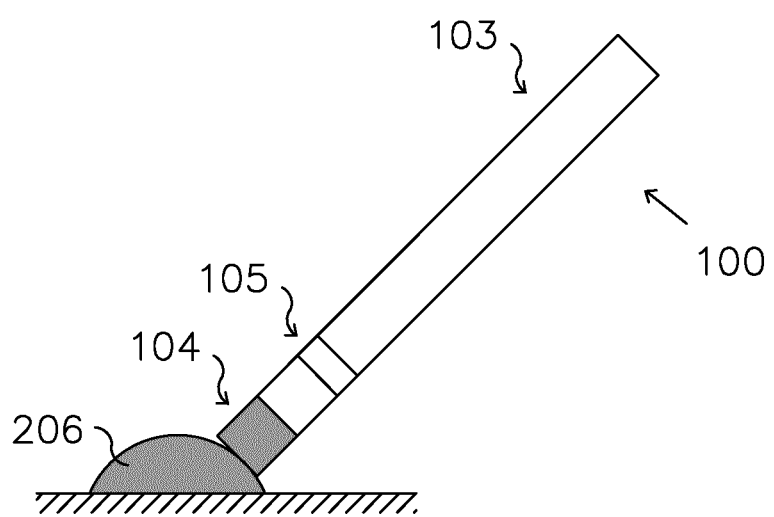
FIG. 2A to FIG. 2E illustrate use of the sample transfer device.
Figure 2B:
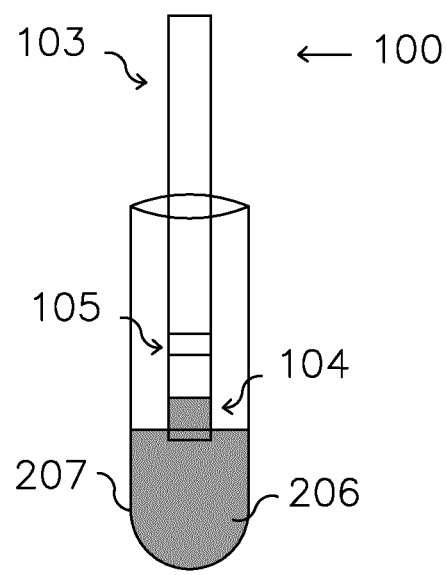
Figure 2C:
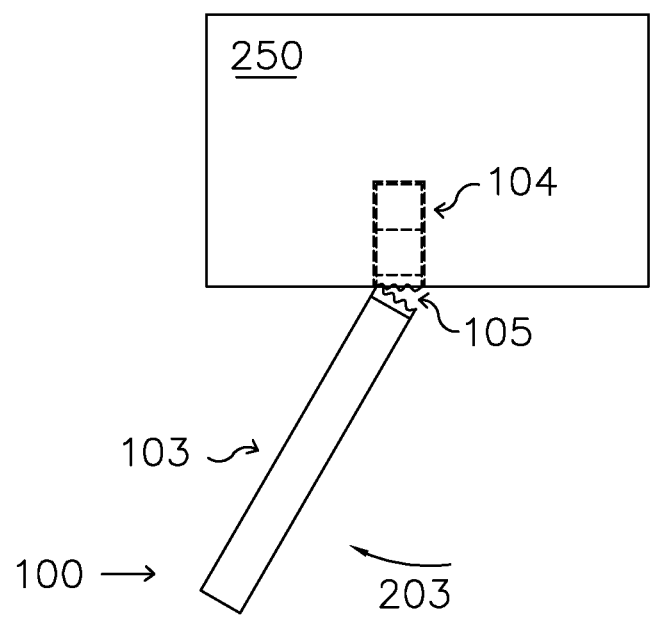
Figure 2D:
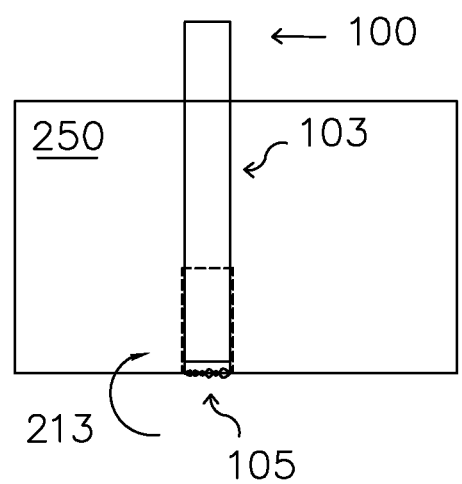
Figure 2E:
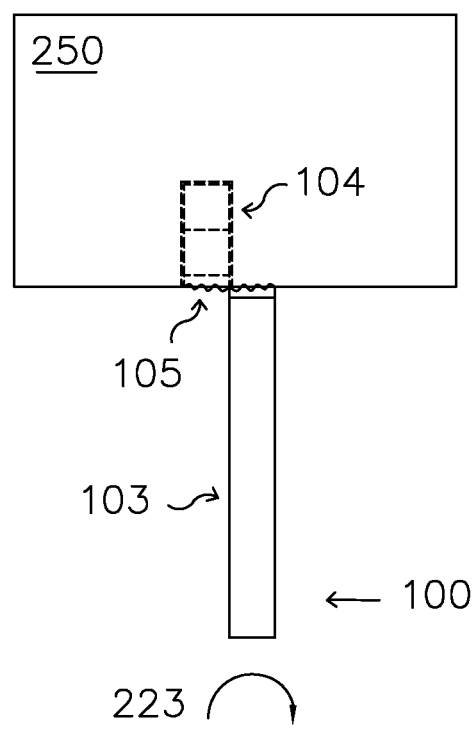

With reference to FIG. 1, a sample transfer device 100 for receiving and holding a liquid sample is described. The sample transfer device 100 comprises an elongate body having a first end 101 opposed to a second end 102 in the elongate direction 111. A handling portion 103 disposed at the first end 101 is arranged to provide for gripping and handling means. A sample collecting portion 104 disposed at the second end 102 is arranged to provide for means to receive a volume of the liquid sample. A frangible portion 105 disposed between the handling portion 103 and the sample collecting portion 104 is configured to enable complete separation of the sample collecting portion 104 from the sample transfer device 100. In preferred embodiments, the frangible portion 105 is configured to break when the sample collecting portion 104 is secured and the sample transfer device 100 is mechanically deformed along the frangible portion 105.

In use, the elongate body of the sample transfer device 100 allows for a comfortable distance between the handling portion 103 and the liquid sample during collection and transfer of the sample. This prevents contaminations, from or to the liquid sample, and exposure of the user to potentially hazardous substances present in the sample. In preferred embodiments, the distance of the frangible portion 105 to the first end 101 of the elongated body, i.e. the length of the handling portion 103, is larger than the distance of the frangible portion 105 to the second end 102 of the elongate body, where the sample collecting portion 104 is positioned. In another preferred embodiment, the distance of the frangible portion 105 to the first end 101 is at least three times the distance of the frangible portion 105 to the second end 102. It will be apparent to the person skilled in the art that it is possible to increase the length of the handling portion 103 using extensions with additional parts connecting to the handling portion 103 of the sample transfer device 100. For these alternatives, the length of the handling portion is considered as the full length in the elongate direction 111 including the extension, or extensions, used.

Samples to be handled with the sample transfer device 100 may be of diverse types and origins such as, for example, biological samples including urine, blood, serum, sputum and saliva, environmental samples such as water and air condensates, food samples such as beverages and diverse sauces, or cosmetic samples such as fragrances and emulsions. Samples of solid nature can also be handled with the sample transfer device 100, provided a first liquefaction step is performed in order to produce a liquid flowing medium such as for example a solution, a suspension or an emulsion.

Operation of the sample transfer device 100 is now described with reference to FIG. 2A to FIG. 2E. In a first step, the sample collecting portion 104 of the sample transfer device 100 contacts a liquid surface. The liquid 206 can be presented as a drop (FIG. 2A) such as for example, a blood drop formed from a finger prick or a condensation drop formed on a cold surface. Alternatively, the liquid 206 may be presented inside a container 207 (FIG. 2B), such as for example a vial or a test tube. A liquid sample is drawn into the sample collecting portion 104 of the sample transfer device 100.

Once the liquid sample has been collected, it is retained inside the sample collecting portion 104 during handling. In a subsequent step, the sample transfer device 100 is mechanically deformed along the frangible portion 105 until rupture or fracture. At this point the sample collecting portion 104 is completely separated from the sample transfer device 100. The mechanical deformation along the frangible portion 105 leading to breaking of the sample transfer device 100 and separation of the sample collecting portion 104 from the sample transfer device 100 may be achieved, for example, by tearing (illustrated in FIG. 2C as movement 203), folding back (illustrated in FIG. 2D as movement 213), or twisting (illustrated in FIG. 2E as movement 223) the handling portion 103 relative to the sample collecting portion 104. Preferably, the sample collecting portion 104 is secured against movement in at least one direction, when the handling portion 103 is moved partially or totally in that same direction. This can be achieved, for example, inserting the sample collecting portion 104 into a slot or into a confining housing 250 prior to mechanically deforming the sample transfer device 100 along the frangible portion 105 to promote complete separation of the sample collecting portion 104 from the sample transfer device 100.

The frangible portion 105 typically comprises a reduction in the resisting cross section of the sample transfer device 100. Additionally, the frangible portion 105 is configured to resist mechanical loading during sample collection and handling when the sample transfer device 100 is mostly unconstrained and also to resist mechanical stresses arising during insertion into a slot or confining housing 250. The reduction in the resisting cross section of the sample transfer device 100 may be provided as a notch or as a through cut to yield separate cross sections of smaller dimensions. The main purpose of the reduction in resisting cross section is to favour localised deformation leading to rupture at the frangible portion 105, when the sample collecting portion 104 is constrained against movement in at least one direction and the sample transfer device 100 is mechanically loaded in that direction.

Alternative configurations of the frangible portion 105 in accordance with different embodiments of the sample transfer device 100 are now described with reference to FIGS. 3A to 3G. The frangible portion 105 may comprise one or more perforations through the thickness of the elongate body. Thickness is to be understood as the smallest dimension of the sample transfer device 100 which is typically perpendicular to the elongate direction 111. Thickness direction 311, is to be understood as the direction along the thickness. Moreover, perforations are to be understood as cuts through the thickness and may or may not involve removal of material. For example, perforations may be punctures or linear cuts without material removed or cut out areas of a given shape with material removed.

Figure 3A:
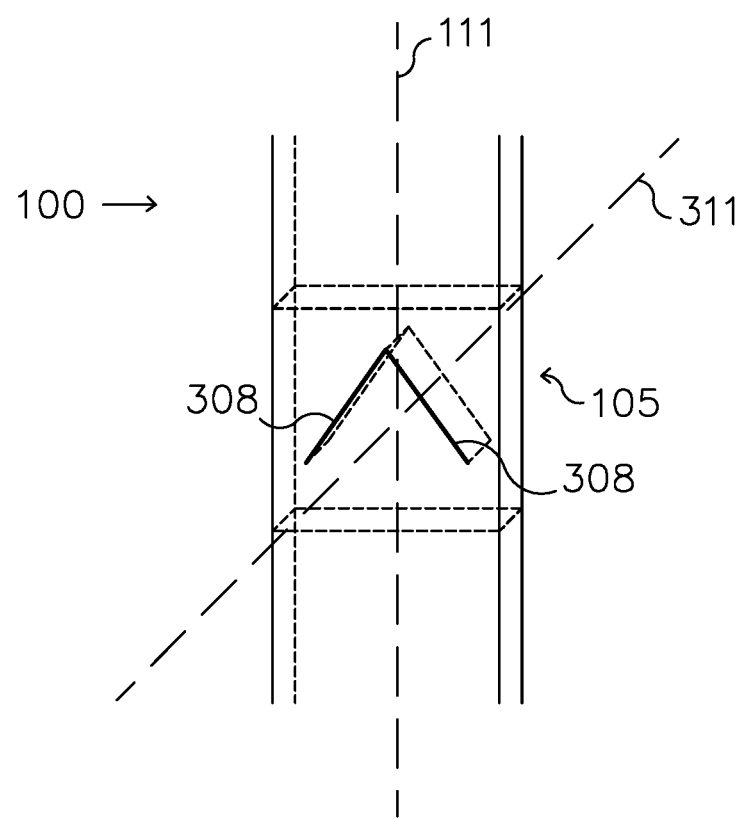
FIG. 3A to FIG. 3G illustrate alternative configurations of the frangible portion in accordance with different embodiments of the sample transfer device.
Figure 3B:
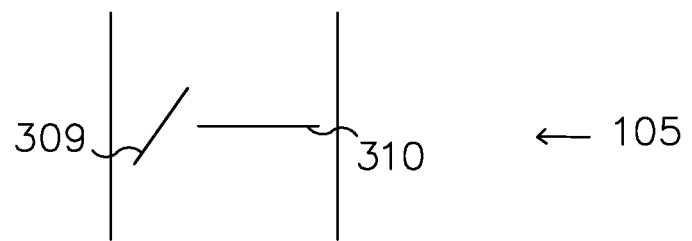
Figure 3C:
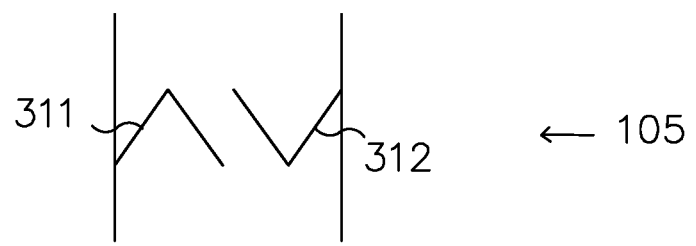
Figure 3D:
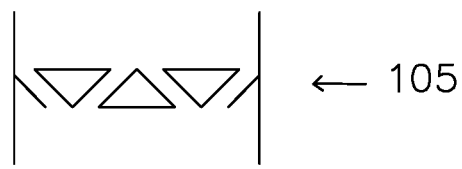
Figure 3E:
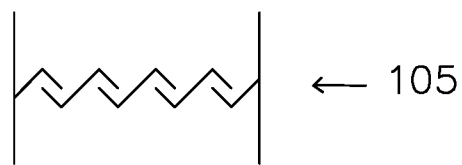
Figure 3F:
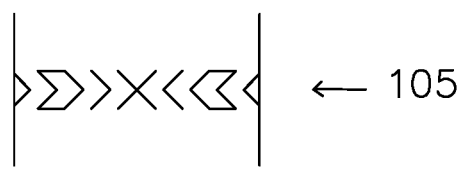
Figure 3G:
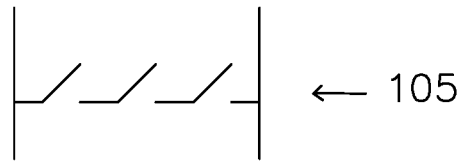

In some embodiments (FIG. 3A), the frangible portion 105 comprises one perforation 308 through the thickness of the elongate body extending in at least two different directions perpendicular to the thickness direction 311. In other embodiments, the frangible portion 105 comprises at least two perforations through the thickness of the elongate body of the sample transfer device 100. FIG. 3B illustrates one such embodiment in which perforation 309 extends in a first direction perpendicular to the thickness direction 311 (out of the plane), and perforation 310 extends in a second direction also perpendicular to the thickness direction 311 (out of the plane) and different from the first direction. FIG. 3D illustrates other such embodiment in which each of the at least two perforations 311 and 312 extends in at least two directions perpendicular to the thickness direction 311 (out of the plane). In yet further embodiments (FIG. 3D to FIG. 3G), the frangible portion 105 comprises multiple perforations. In some embodiments, the perforations may have different shapes or the same shape disposed in different orientations.

Alternative configurations of the sample collecting portion 104 in accordance with different embodiments of the sample transfer device 100 are now described with reference to FIG. 4 to FIG. 8. The sample collecting portion 104 comprises at least one surface configured to be wetted by the liquid sample. In some embodiments, the surface configured to be wetted by the liquid sample may be hydrophilic, i.e., wetted by aqueous media. In other embodiments the surface may be lipophilic, i.e., wetted by oils and fats. In other embodiments, the surface configured to be wetted by the liquid sample is comprised within a liquid absorbent material. For example, the surface configured to be wetted by the liquid sample may be defined as the internal structure of porous material such as, for example, filter pads, membrane pads and woven or non-woven fabric pads. A pad is to be understood as a flat piece of a liquid absorbent material. In such embodiments, samples are absorbed by the porous material and the overall pad dimensions and internal pore structure determine the maximum volume of sample collected. In some embodiments, a cavity with a wall providing a hydrophilic surface may be combined with such a pad.

Figures 4A, 4B:
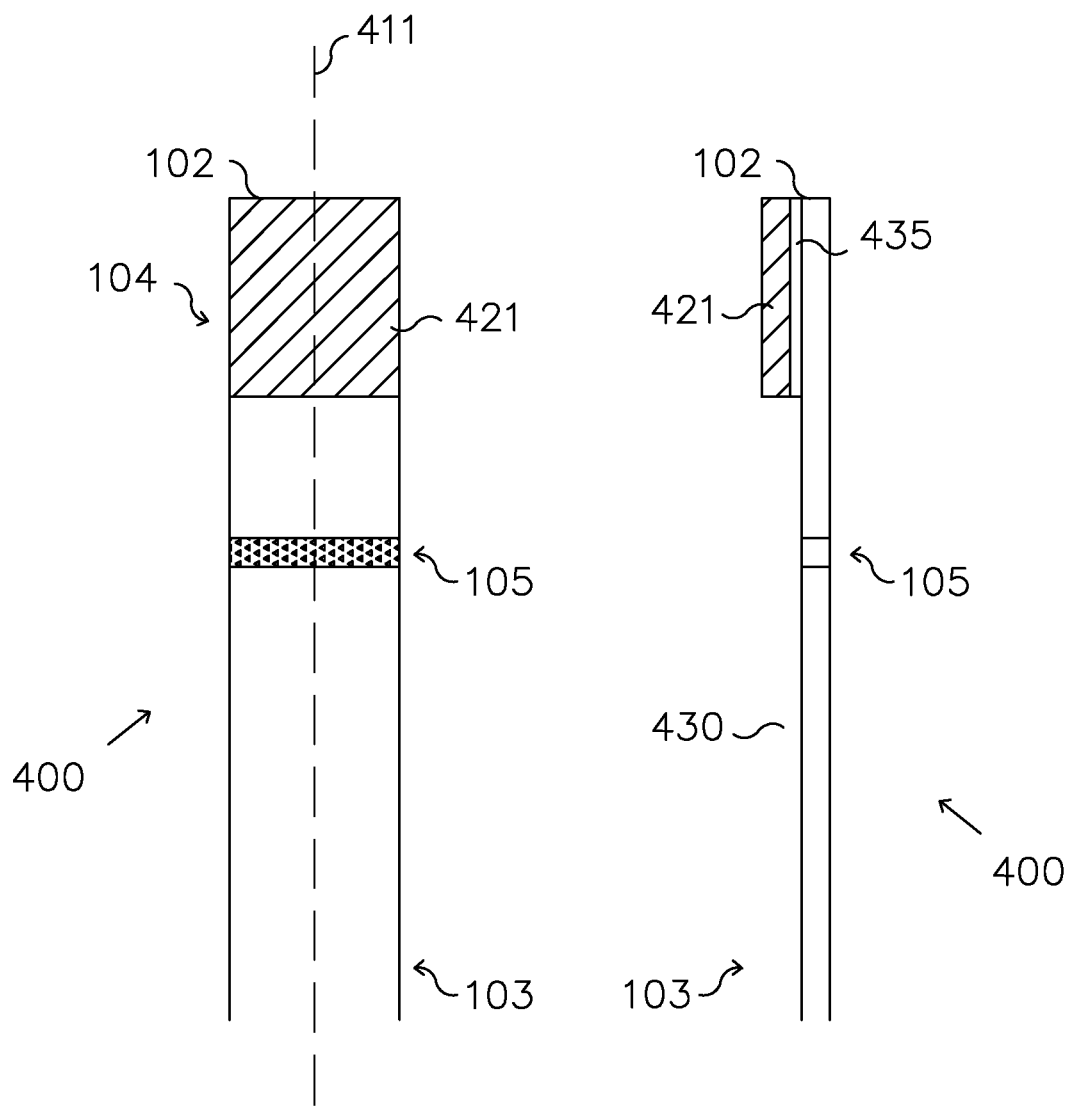
FIG. 4A to FIG. 4B illustrate a configuration of the sample collecting portion in accordance with embodiments of the sample transfer device.

FIG. 4A illustrates a sample transfer device 400 comprising a handling portion 103, a sample collecting portion 104 and a frangible portion 105. FIG. 4B illustrates a cross sectional view of the sample transfer device 400 along the elongate direction 411. The sample collecting portion 104 comprises a surface 421 configured to be wetted by the liquid sample. Surface 421 is comprised within a liquid absorbent pad.

Figures 5A, 5B:
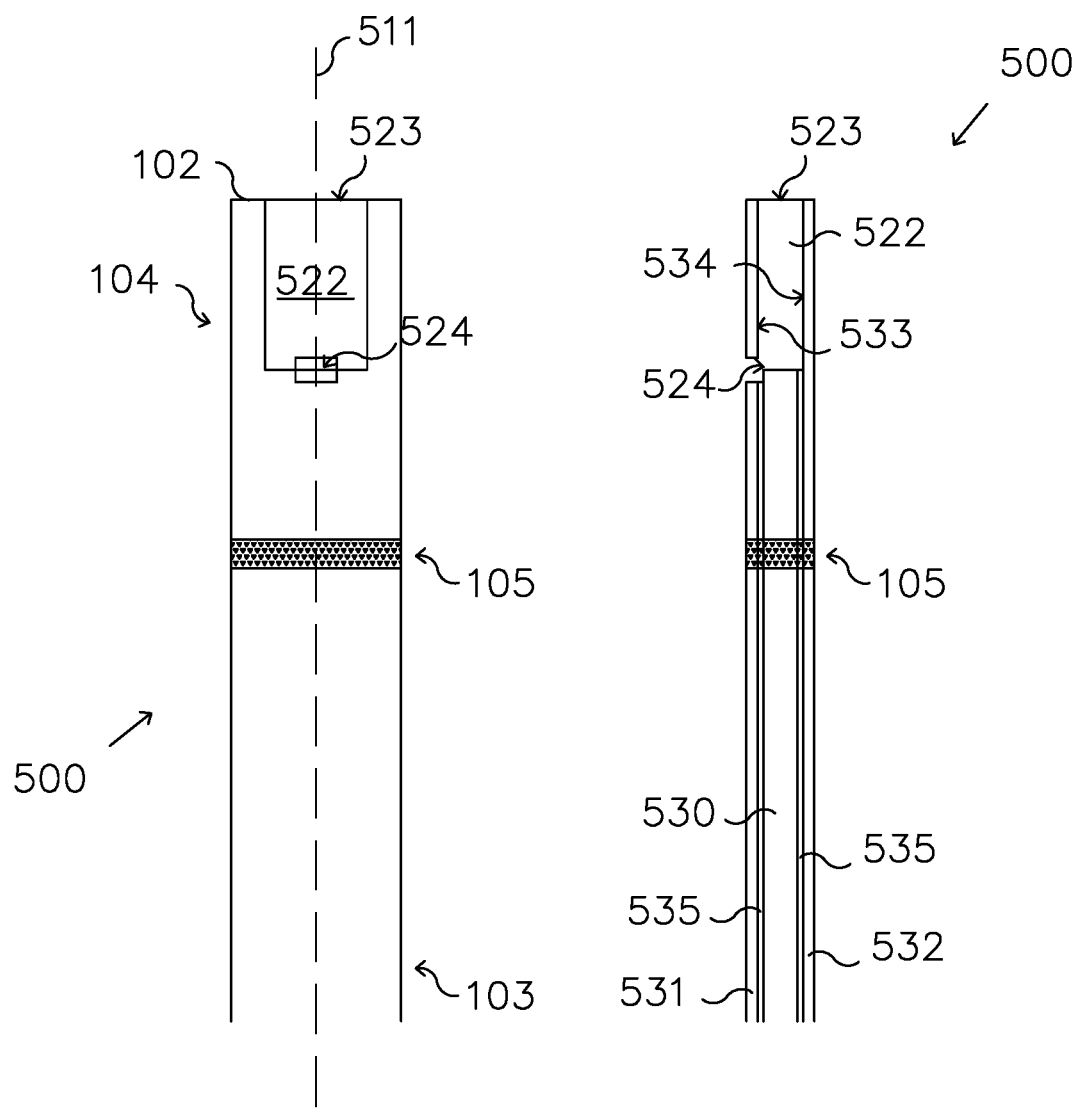
FIG. 5A to FIG. 5B illustrate another configuration of the sample collecting portion in accordance with embodiments of the sample transfer device.

In other embodiments, the sample collecting portion 104 of the sample transfer device 100 comprises at least one cavity. The at least one cavity comprises at least one aperture serving as inlet port for the liquid sample and at least one other aperture to act as an air vent as the sample fills the cavity. FIG. 5A illustrates a sample transfer device 500 comprising a handling portion 103, a sample collecting portion 104 and a frangible portion 105. The sample collecting portion 104 comprises a cavity 522. Cavity 222 comprises an inlet port 523 and an air vent 524.

In some of these embodiments, the at least one cavity is defined between two opposite and substantially parallel inner surfaces, wherein one or both inner surfaces are configured to be wetted by the liquid sample. FIG. 5B illustrates a cross sectional view of the sample transfer device 500 along the elongate direction 511. The sample collecting portion 104 comprises a cavity 522 defined between two opposite and substantially parallel inner surfaces 533 and 534. Cavity 522 further comprises an inlet port 523 and an air vent 524. Provided one or both inner surfaces 533 and 534 are configured to be wetted by the liquid sample, the liquid sample is drawn by capillary action through the inlet port 423 into the cavity 422 when the sample collecting portion 104 is brought in contact with a liquid surface.

The geometry of cavity 522 may be defined as a perforation through spacer layer 530 positioned between a first 531 and second 532 outer layers. Each of the outer layers 531 and 532 define inner surfaces 533 and 534, respectively, of the cavity 522. The maximum sample volume collected is determined by the geometry and dimensions of the cavity 522 and the position of the apertures serving as the inlet port 523 and the air vent 524. The different layers of the sample transfer device 500 may, in some embodiments, be arranged in a laminate comprising additional adhesive material (intermediate) layers 535 to bond the first 531 and second 532 outer layers to the spacer layer 530.

In yet further embodiments of the sample transfer device 100, the sample collecting portion 104 may comprise more than one surface configured to be wetted by the liquid sample to allow for collecting more than one volume of a liquid sample or different liquid samples. In this manner, it is possible to use the same sample transfer device to transfer more than one volume of a liquid sample or different samples.

Figure 6:
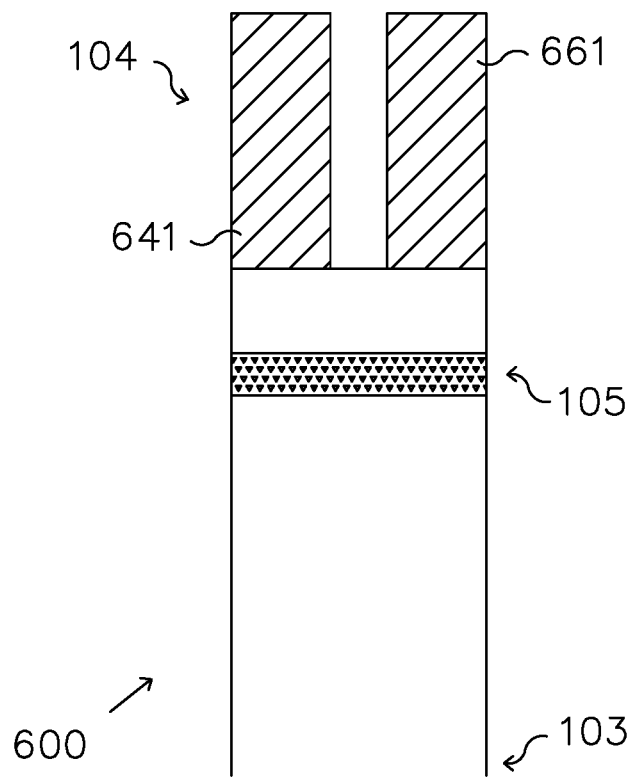
FIG. 6 illustrates an alternative configuration of the sample collecting portion in accordance with embodiments of the sample transfer device.
Figure 7:
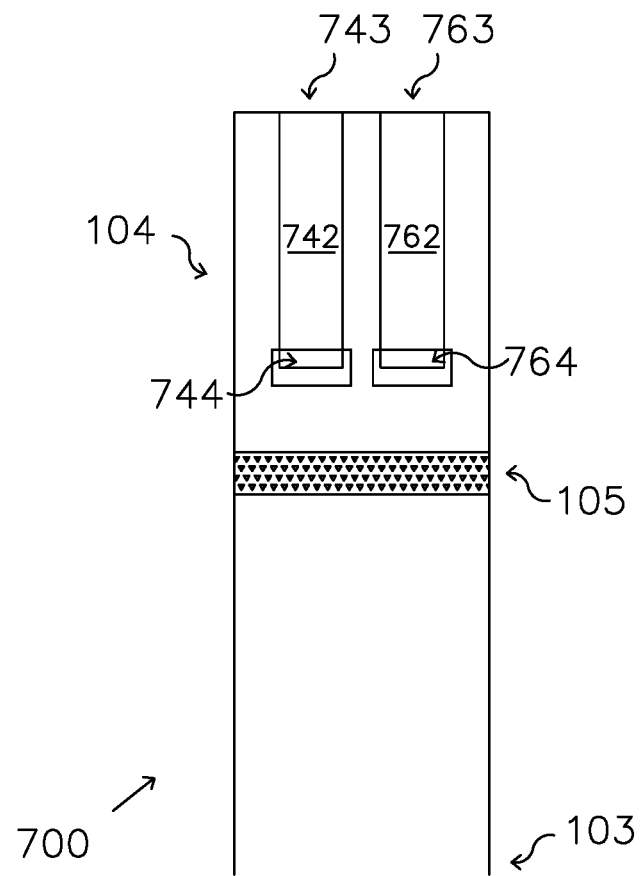
FIG. 7 illustrates another alternative configuration of the sample collecting portion in accordance with embodiments of the sample transfer device.

FIG. 6 illustrates a sample transfer device 600 comprising a handling portion 103, a sample collecting portion 104 and a frangible portion 105. The sample collecting portion 104 comprises two separate liquid absorbent pads 641 and 661. FIG. 7 illustrates a sample transfer device 700 comprising a handling portion 103, a sample collecting portion 104 and a frangible portion 105. The sample collecting portion 104 comprises two separate cavities 742 and 762. Each one of these cavities having a respective inlet port 743 and 763 and a respective air vent 744 and 764. Optionally, the same air vent may be shared by the two cavities 742 and 762 (not shown).

Figure 8A:
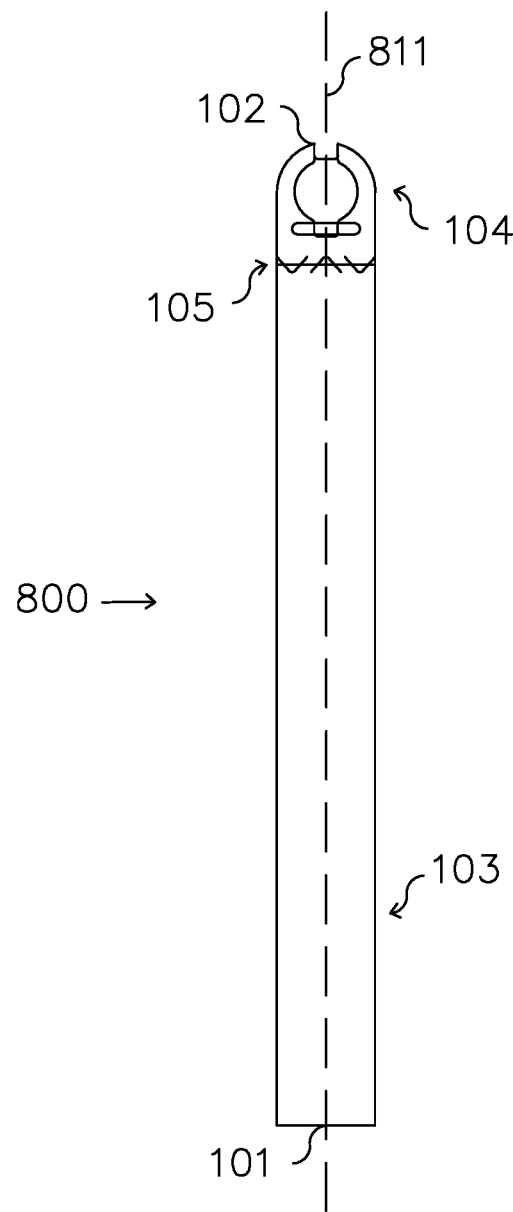

Other preferred embodiments of the sample transfer device will now be described with reference to FIGS. 8A to 8E. FIG. 8A illustrates a sample transfer device 800 for receiving and holding a liquid sample. The sample transfer device 800 comprises an elongate body having a first end 101 opposed to a second end 102. A handling portion 103 disposed at the first end 101 is arranged to provide for gripping and handling means. A sample collecting portion 104 disposed at the second end 102 is arranged to provide for means to receive a volume of the liquid sample. A frangible portion 105 disposed between the handling portion 103 and the sample collecting portion 104 is configured to enable complete separation of the sample collecting portion 104 from the sample transfer device 800. The frangible portion 105 is configured to break when the sample collecting portion 104 is secured and the sample transfer device 800 is mechanically deformed along the frangible portion 105.

Figure 8B:
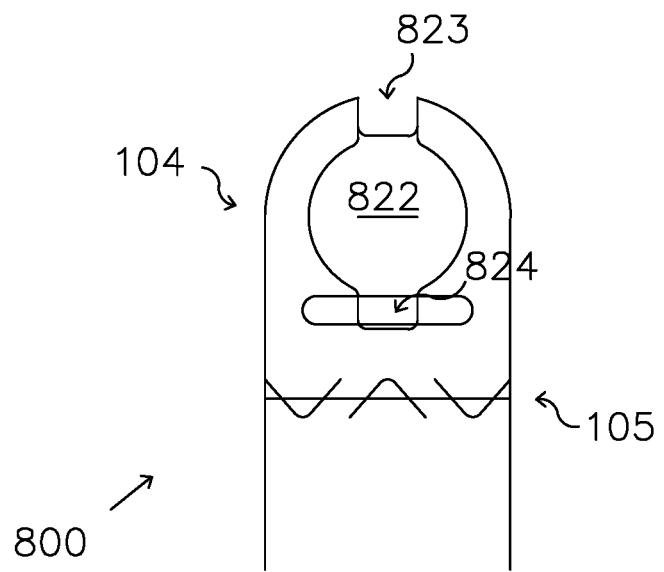

With reference to FIG. 8B, the sample collecting portion 104 of the sample transfer device 800 comprises a cavity 822 of a substantially circular shape. This improved configuration facilitates capillary filling and at the same time provides a familiar shape to determine sample sufficiency. The cavity 822 is defined by two opposing and substantially parallel inner surfaces provided by a first outer layer 831 (FIG. 8C) and a second outer layer 832 (FIG. 8E) and a perforation through a spacer layer 830 (FIG. 8D) disposed intermediate the outer layers. The thickness of the spacer layer 830 is preferably below 1 mm or even below 0.5 mm. It should be noted that confining a given volume in thinner cavities results in larger sample areas which are easier to analyse with regard to sample sufficiency. It may also be advantageous that the first outer layer 831 and the second outer layer 832 are provided in a transparent material. Alternatively, the respective one or both inner surfaces may exhibit a certain haze to transparency, and loose haziness as the cavity 822 is filled with liquid. This latter effect is particularly useful when handling transparent samples as it helps to ascertain the filling of cavity 822.

Figure 8F:
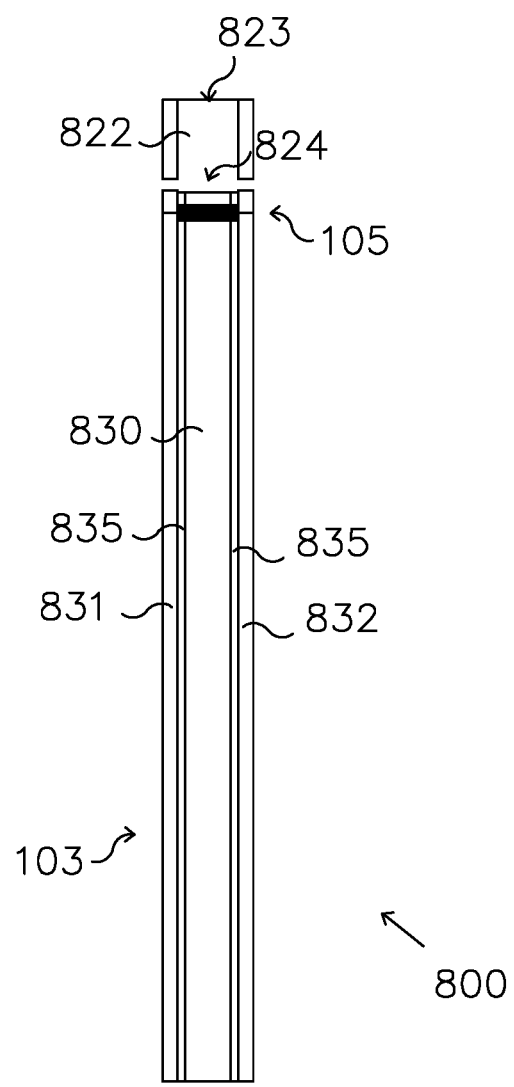

FIG. 8F illustrates a cross sectional view of the sample transfer device 800 along the elongate direction 811. The air vent 824 is substantially coincident with perforations 871 (FIG. 8C) and 872 (FIG. 8E) through the outer layers 831 and 832, respectively. In improved configurations, there is a partial or total overlap between perforations 871 and 872. Similarly, the inlet port 823 is substantially coincident with perforations 881 (FIG. 8C) and 882 (FIG. 8E) through the outer layers 831 and 832, respectively. Also in this case, a partial or total overlap between the perforated areas of both layers is advantageous. The overlap between perforations 871 and 872 and perforations 881 and 882 prevents the liquid sample to be removed from the cavity 822 through the inlet port 823 or through the air vent 824, when a tissue paper or other absorbing medium is used to clean the external surface of the sample transfer device 800. In these cases, it may be further advantageous that both inner surfaces of the first and second outer layers 831 and 832 are wetted by the liquid sample.

Figure 9:
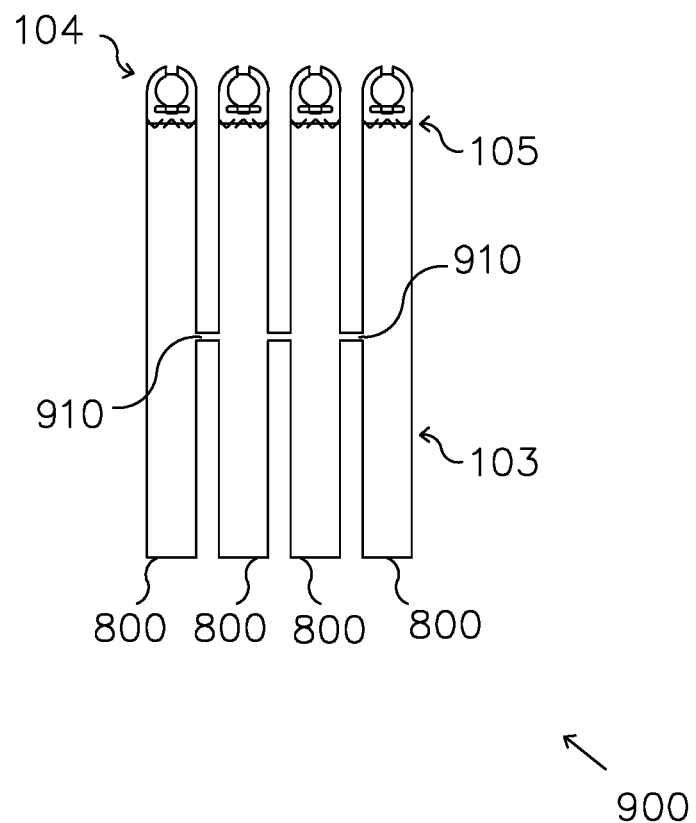
FIG. 9 illustrates a set of attached sample transfer devices.

With reference to FIG. 9, a set of attached sample transfer devices 900 comprises a plurality of sample transfer devices 800 arranged in a row. It will be appreciated that sample transfer devices 100, 400, 500, 600 and 700 can be arranged in a similar fashion. In set 900, pairs of adjacent sample transfer devices 800 are connected to each other by at least one frangible connection 910. The frangible connection 910 may be broken to separate a sample transfer device 800 from the set 900 to enable it to be used. The frangible connection 910 may preferably be positioned in the handling portion 103 of the sample transfer device 800 away from the frangible portion 105 to avoid mechanical deformation or premature weakening of the frangible portion 105.

In some embodiments, the plurality of sample transfer devices in set 900 do not need to be identical. The set 900 may comprise a plurality of sample transfer devices arranged in a plurality of rows and columns. In any given row, pairs of adjacent sample transfer devices are connected to each other by at least one frangible connection 910. Between rows pairs of adjacent sample transfer devices are connected to each other by at least one frangible connection 910.

Figure 10:
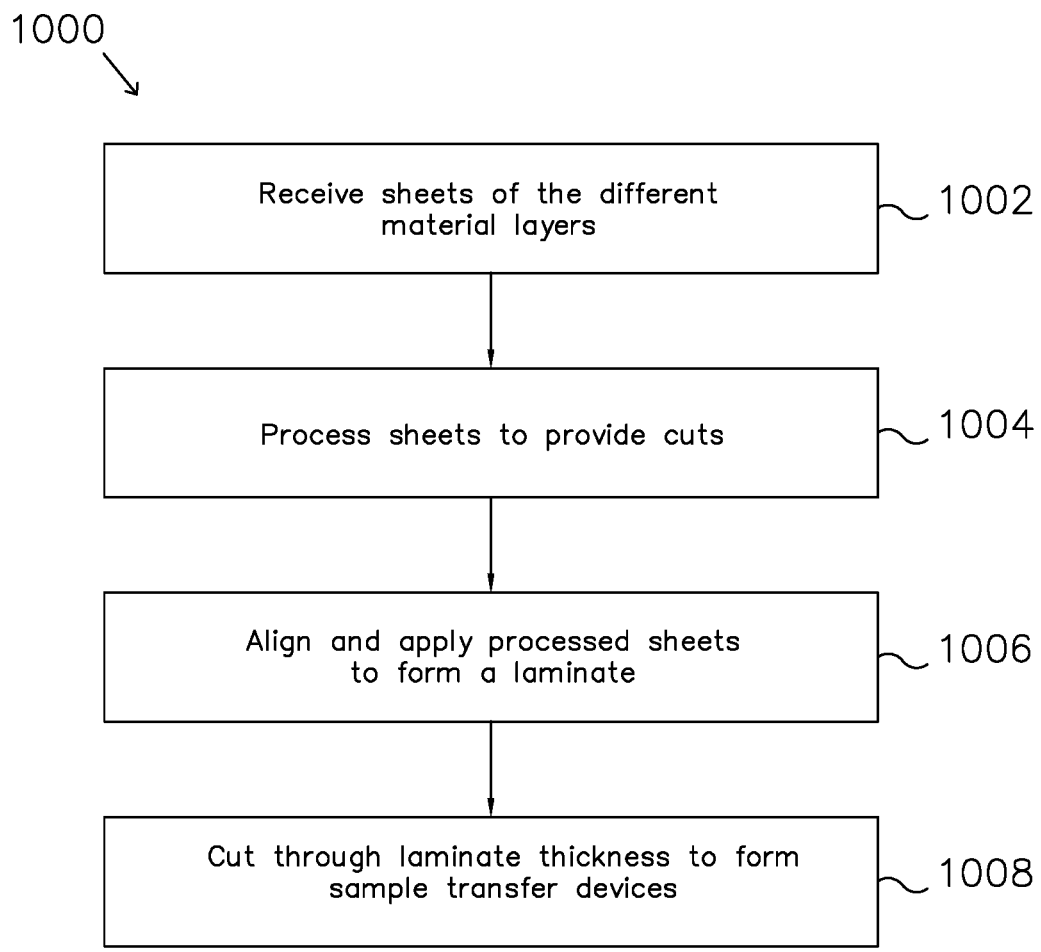
FIG. 10 illustrates a method of manufacturing a plurality of sample transfer devices.

A method of manufacturing a plurality of sample transfer devices 500, 700 and 800 is now described with reference to FIG. 10. The method 1000 comprises in a first step 1002 receiving one sheet of spacer material, two sheets of outer layer material, and two sheets of adhesive material to be disposed intermediate the outer layer material and the spacer material in the final laminate. One or both of the outer layer material sheets have at least one side configured to be wetted by the liquid sample. For example, one side having been pre-treated to exhibit a hydrophilic character. At step 1004, the adhesive sheets are first applied on either side of the spacer material to form what is commonly referred to as a spacer tape. The spacer tape is then perforated to define the geometry of the cavity (or cavities) 522, 742, 762, 822 of the sample collecting portion 104. At this step, at least one sheet of the outer layer material is perforated to provide for the air vent (or vents) 524, 744, 764, 824 of the sample collecting portion 104. Optionally, further perforations on the same or both sheets of outer layer material may be performed in the same cutting action. For example, additional perforations for inlet ports 523, 743, 763, 823 and frangible portion 105 may also be executed at this step.

Subsequently, at step 1006, the sheets of outer layer material with the hydrophilic side oriented towards the spacer tape are aligned and applied to the spacer tape to form a laminate construction comprising a plurality of uncut sample transfer devices. The plurality of uncut sample transfer devices may be arranged in various ways, for example in one or more rows or one or more orientations. A final cutting step 1008 through the laminate thickness, then yields either separate sample transfer devices or sets of attached sample transfer devices with frangible connections between adjacent pairs as described with reference to FIG. 9. It is also possible to perform the perforations of the frangible portion 105 of the sample transfer devices only in step 1008, in the same cutting action. In some embodiments, the spacer tape is provided with a perforation for the cavity (or cavities), and laminated together with the outer layers. Subsequent to this lamination step, perforations are then made in the resulting laminate to form the air vent and inlet port by perforating through all five sandwiched layers (outer—intermediate—spacer—intermediate—outer), thereby ensuring alignment of the perforations for the inlet port and air vent.

Method 1000 is equally applicable for manufacturing sample transfer devices 400 and 600, comprising a liquid absorbent material 421, 641, 661 in the sample collecting portion 104. In step 1002 the method comprises receiving one sheet of a backing material (for example the same as the spacer material), one sheet of adhesive material and one sheet of liquid absorbent material. In step 1004, the two sheets of adhesive and liquid absorbent material 510 are cut through thickness to provide strips having substantially the same width. The two strips are aligned together and applied to the backing material sheet in step 1006. Similar to the above description, a final cutting step 1008 then yields either separate sample transfer devices or sets of attached sample transfer devices with frangible connections between adjacent pairs. At this step the perforations of the frangible portion 105 are also executed in the same cutting action.

The application of the different material layers to each other may be carried out by roll lamination or flat press bonding either with discrete sheets or with roll to roll converting systems. Perforations as well as final cuts may be provided by die cutting, kiss cutting or laser cutting either in batch or continuous processes. Preferably, all steps are integrated in a roll to roll process for increased manufacturing efficiency, in which case the sheets corresponding to the different material layers are supplied in roll format. The manufacturing method 1000 enables quick and easy manufacture of a plurality of sample transfer devices. In those embodiments where frangible connections remain, the method provides a convenient way of supplying a plurality of attached sample transfer devices in multiple unit sets.

Figure 11:
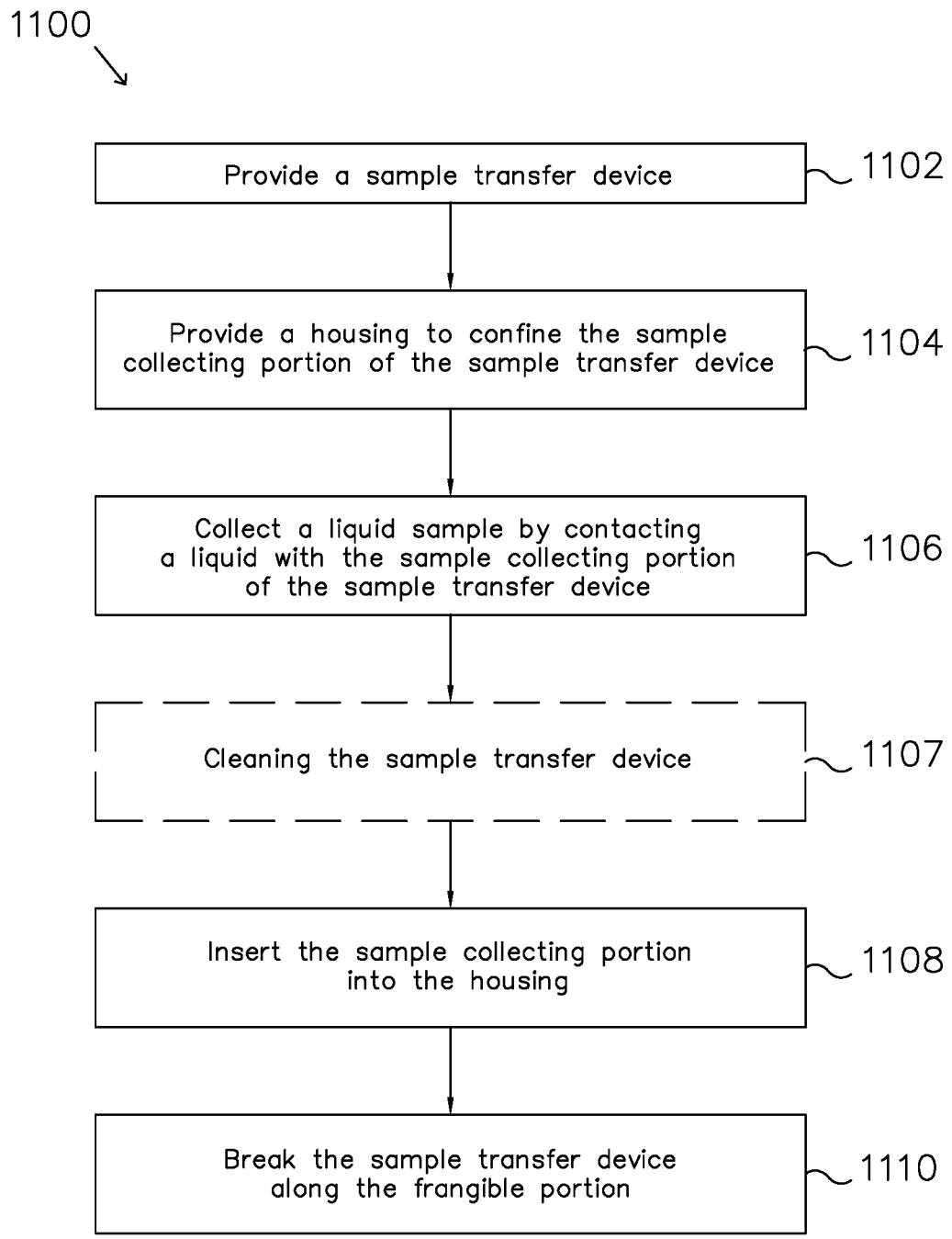
FIG. 11 illustrates a method for collecting and transferring a liquid sample using the sample transfer device.

With reference to FIG. 11, a method 1100 of using the sample transfer device 100 for collecting and transferring liquid samples to a separate housing is now described. At step 1104, a housing is provided to confine the sample collecting portion 104 of the sample transfer device 100. Subsequently at step 1106, the method 1100 further comprises contacting a liquid with the sample transfer device 100 to collect the sample by wetting at least one surface of the sample collecting portion 104. At step 1108, the sample collecting portion 104 of the sample transfer device 100, is inserted into the housing to confine the sample collecting portion 104 and constrain movement in at least one direction. At step 1110, a movement of the handling portion 103 of the sample transfer device 100 in the at least one direction induces mechanical deformation and breaks the sample transfer device 100 along the frangible portion 105 to leave the sample collecting portion 104 filled with sample inside the housing. The method 1100 may be performed using any of the sample transfer devices 400, 500, 600, 700 and 800.

The method 1100 may include an additional step 1107, for cleaning excess liquid sample from the outer surface of the sample transfer device 100 after collecting the liquid sample and before inserting the sample collecting portion 104 of the sample transfer device 100 into housing. This step is particularly useful when collecting samples from vials and test tubes as the sample collecting portion 104 may be dipped below the liquid surface and an excess of liquid wets the outer surface of the sample transfer device 100, which may contaminate the housing during insertion.

Figure 12:
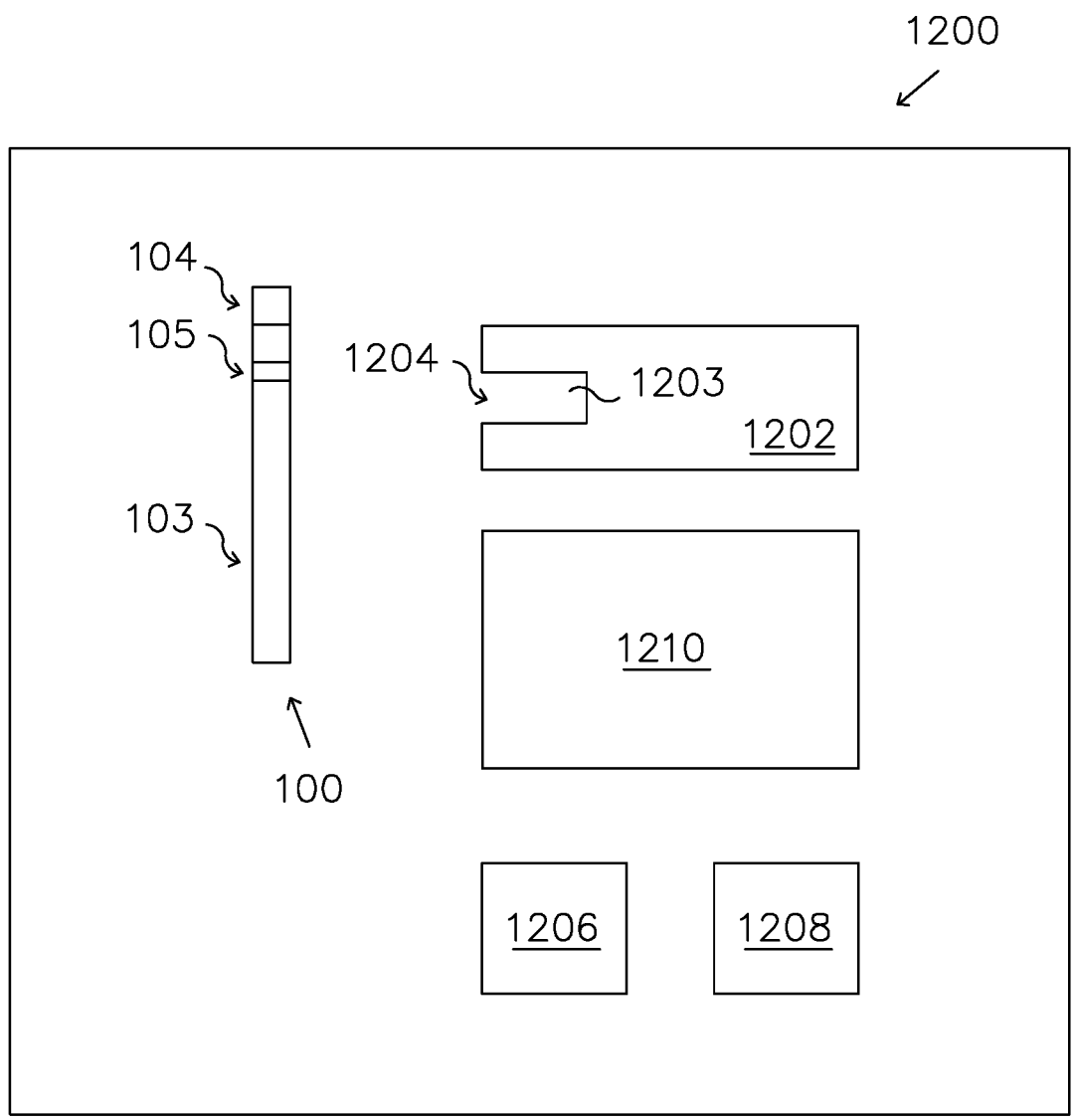
FIG. 12 illustrates a system for handling liquids comprising the sample transfer device.

With reference to FIG. 12, a system 1200 for handling liquid samples is now described. The system 1200 comprising the sample transfer device 100 and a device for processing liquid samples 1202, a processor 1206, a controller 1208 and means 1210 to drive liquid flow inside the device for processing liquid samples 1202. Means to drive and control liquid flow inside devices for processing liquid samples are common in the art and include the use pneumatic or vacuum pumps to generate gas pressure differentials, DC motors to generate centrifugal pressure differentials by rotation, and surface tension gradients to generate capillary pressure differentials. The system 1200 may comprise any of the sample transfer devices 400, 500, 600, 700 and 800.

The device for processing liquid samples 1202 is provided with an aperture 1204 in communication with at least one receiving cavity 1203, wherein the at least one receiving cavity is configured to receive and retain the sample collecting portion 104 of the sample transfer device 100. In some embodiments, the sample collecting portion 104 of the sample transfer device 100 and the receiving cavity 1203 of the device for processing liquid samples 1202 are configured to provide for a tight (or interference) fit in at least one direction in order to secure the sample collecting portion 104 during separation from the sample transfer device 100. Preferably, when the sample collecting portion of the sample transfer device is inserted in the receiving cavity 1203 and secured in position, the frangible portion 105 is positioned near or at an edge of aperture 1204, so as to further facilitate breaking the sample transfer device 100 along the frangible portion 105.

Figure 13A:
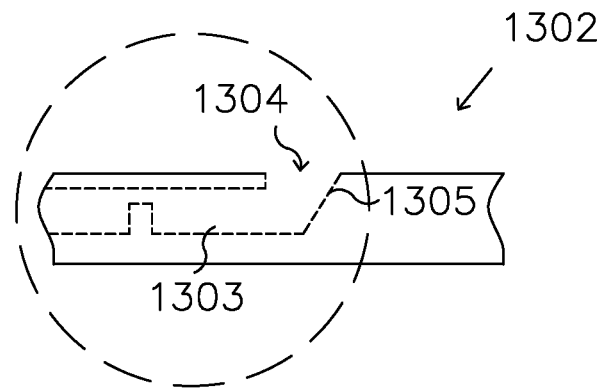
FIG. 13A to FIG. 13C illustrate a specific configuration of a device for processing liquid samples comprised in the system for handling liquids.

In other embodiments as illustrated in FIG. 13A, the receiving cavity 1303 of the device for processing liquid samples 1302 is arranged as an undercut extending laterally from aperture 1304. This ensures enough travel of the sample collecting portion 104 of the sample transfer device 100 into the device for processing liquid samples 1302 without requiring a significant penetration depth. In other words, the receiving cavity 1303 is disposed substantially parallel and near to an external surface of the device for processing liquid samples 1302. Such embodiments are particularly useful for devices for processing liquid samples configured in thin formats such as for example, lab on chip, lab on a disc or lab on card devices, wherein the device thickness is typically much smaller than other device dimensions. As a consequence, the allowed penetration depth is minimal and typically below 1 or 2 mm. In these cases, the sample transfer device 100 must exhibit flexibility as it needs to bend in order to slide in the laterally disposed undercut defining the receiving cavity 1303. Additionally, the frangible portion 105 of the sample transfer device 100 is configured to resist the bending stresses to avoid premature detachment of the sample collecting portion 104 during insertion. Frangible portions 105 with perforations configured as shown in FIGS. 3C to 3G are fit for this purpose. The exact dimensioning of perforations and their spacing takes into account the mechanical properties of the sample transfer device constituent materials.

Figure 13B:
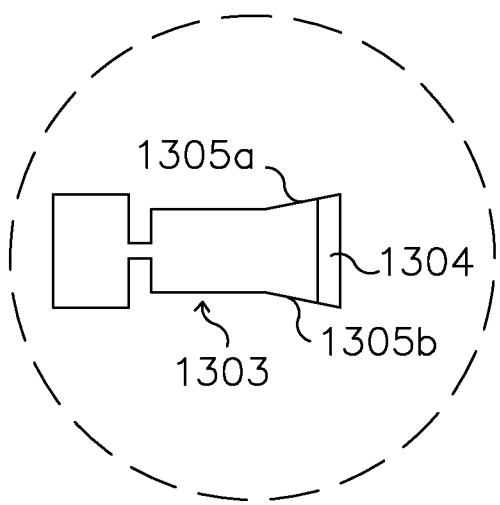

In preferred embodiments as illustrated in FIG. 13B, aperture 1304 in the device for processing liquid samples 1302 is larger than the sample collecting portion cross section to facilitate introduction of the sample collecting portion 104 into the receiving cavity 1303. Additionally, the receiving cavity 1303 is arranged to continuously narrow with smooth surfaces 1305a and 1305b to self-guide the sample collecting portion into a fit position. Alternatively, the sample collecting portion 104 may be narrower at the tip which first enters the device for processing liquid samples 1302, and enlarge to a cross section tight fitting the receiving cavity 1303 in at least one direction. An example of such a sample transfer device is illustrated in FIGS. 8A to 8F. One skilled in the art would combine some of the characteristics above to achieve the same end result of self-guiding the sample collecting portion into a secure position.

Figure 13C:
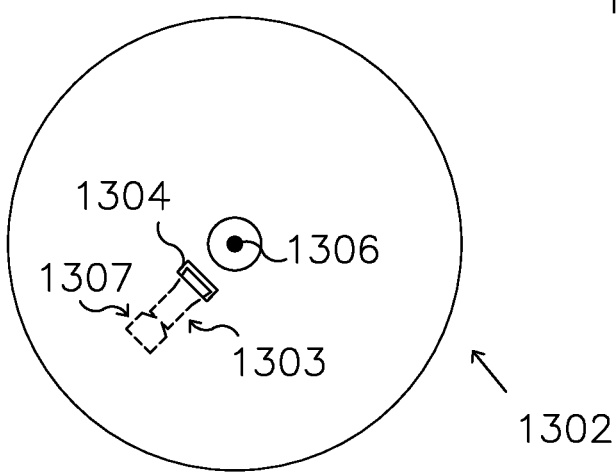

FIG. 13C illustrates an example of a device for processing liquid samples 1302 having a disc shaped body showing an aperture 1304 and a receiving cavity 1303 underneath the surface of the device. The device 1302 is arranged to rotate about the axis of rotation 1306 (out of the plane). In use, after sample collection, the sample collecting portion 104 of the sample transfer device 100 is inserted via aperture 1304 into the receiving cavity 1303. The receiving cavity 1303 is configured for a tight fit with the sample collecting portion 104. When the sample collecting portion is fit into position the frangible portion 105 of the sample transfer device 100 is substantially aligned with the edge of aperture 1304. The handling portion 103 of the sample transfer device 100 is folded back along the frangible connection 105 to break the sample transfer device 100, leaving the sample collecting portion 104 inside the receiving cavity 1303. In preferred embodiments the receiving cavity 1303 is substantially aligned with the radial direction. Rotation of the device 1302 about the axis of rotation 1306 generates a differential pressure in the liquid sample to drive flow of the liquid sample out of the sample collecting portion 104 and into downstream structures of device 1302, such as cavity 1307.

It will be apparent to a person skilled in the art that the receiving cavity 1303 may be positioned in a different orientation relative the radial direction. In other embodiments, the device for processing liquid samples 1302 could be arranged in a configuration other than a disk and the differential pressure to drive flow of the liquid sample out of the sample collecting portion 104 be achieved by other means. For example, a vacuum pump could be used to generate a vacuum pressure through cavity 1307 to extract the liquid sample. In yet another example, a liquid absorbing medium could be disposed in cavity 1307 to contact the inlet port of the sample collecting portion 104 in order to extract the sample by capillary pressure driven flow.

Figure 14:
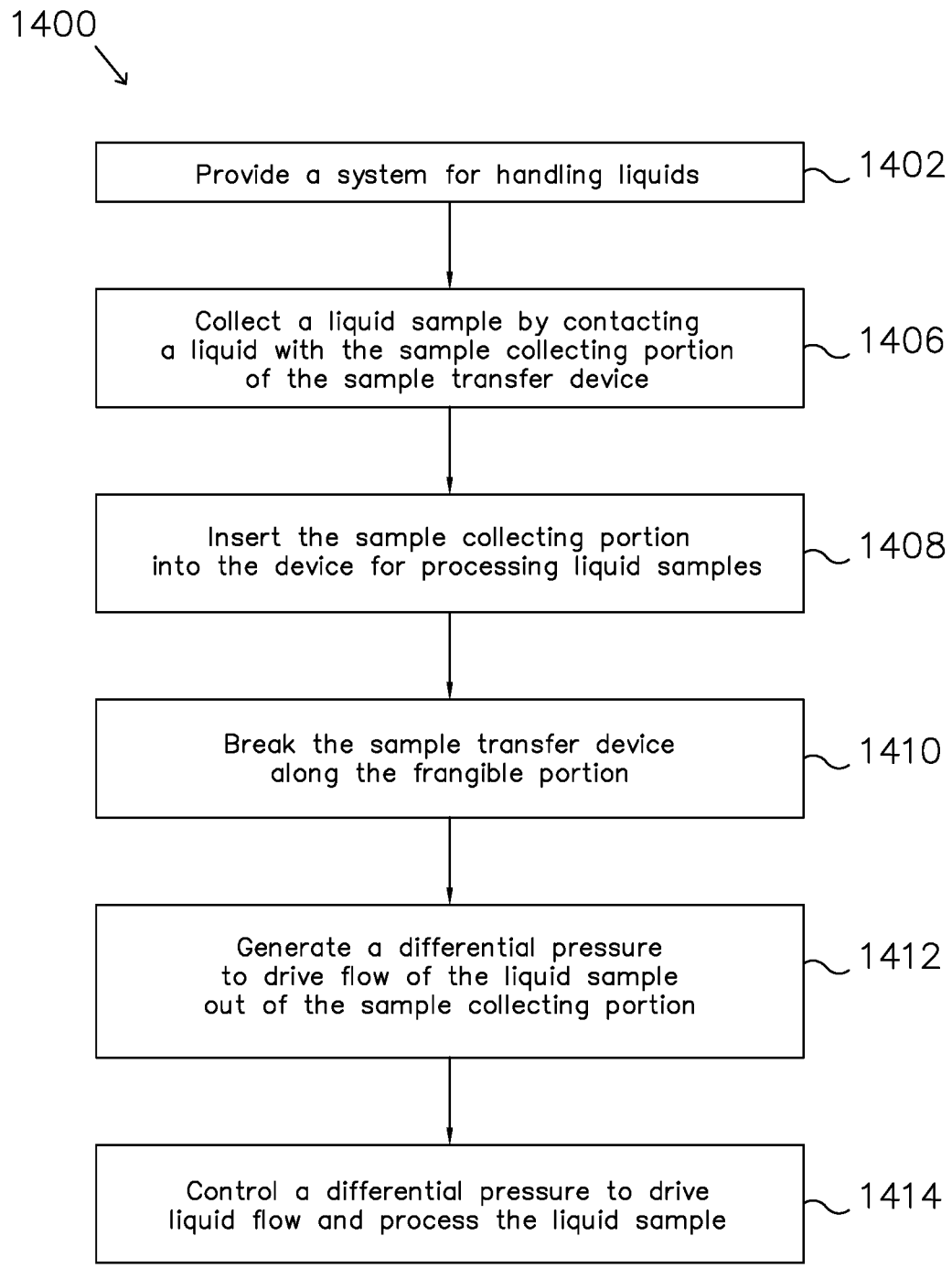
FIG. 14 illustrates a method for collecting, transferring and processing a liquid sample using the system for handling liquids.

With reference to FIG. 14, a method 1400 for collecting, transferring and processing liquid samples is now described. At step 1402, a system for handling liquids 1200 is provided. At step 1406, the method 1400 further comprises contacting a liquid with the sample transfer device 100 to collect the sample by wetting at least one surface of the sample collecting portion 104. At step 1408 the sample collecting portion 104 of the sample transfer device 100, is inserted into the device for processing liquid samples 1202 to confine the sample collecting portion 104 and constrain movement in at least one direction. At step 1410, a movement of the handling portion 103 of the sample transfer device 100 in the at least one direction induces mechanical deformation and breaks the sample transfer device 100 along the frangible portion 105 leaving the sample collecting portion 104 filled with sample inside the device for processing liquid samples 1202. Step 1412, comprises generating a differential pressure to drive flow of the liquid sample out of the sample collecting portion 104 and into the device for processing liquid samples 1202. The method 1400 further comprises step 1414 to control a differential pressure to drive liquid flow inside the device 1202 to process the liquid sample. The differential pressures to drive and control liquid flow in steps 1412 and 1414 may be generated by a variety of means common in the art, including the use pneumatic or vacuum pumps to generate gas pressure differentials, DC motors to generate centrifugal pressure differentials by rotation, and surface tension gradients to generate capillary pressure differentials. Steps 1412 and 1414 may employ different means to generate pressure differentials to drive and control liquid flow during the respective steps.

The method 1400 may include an additional step for cleaning excess liquid sample from the outer surface of the sample transfer device 100 after collecting the liquid sample at step 1406 and before inserting the sample collecting portion 104 of the sample transfer device 100 into device 1202 at step 1408. This additional step is particularly useful when collecting samples from vials and test tubes as the sample collecting portion 104 may be dipped below the liquid surface and an excess of liquid wets the outer surface of the sample transfer device, which may contaminate device 1202 during insertion. The method 1400 may be performed using any of the sample transfer devices 400, 500, 600, 700 and 800.

Figure 15A:
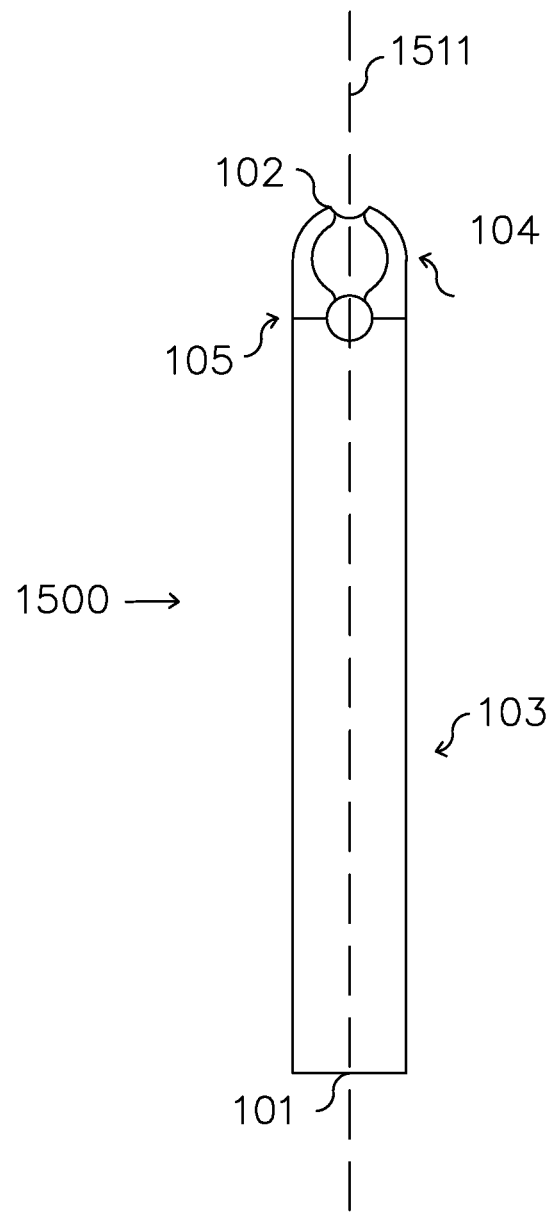

Further embodiments of the sample transfer device will now be described with reference to FIGS. 15A to 15E. FIG. 15A illustrates a sample transfer device 1500 for receiving and holding a liquid sample. The sample transfer device 1500 comprises a handling portion 103 disposed at the first end 101 and a sample collecting portion 104 disposed at the second end 102. A frangible portion 105 disposed between the handling portion 103 and the sample collecting portion 104 is configured to enable complete separation of the sample collecting portion 104 from the sample transfer device 1500.

Figure 15B:
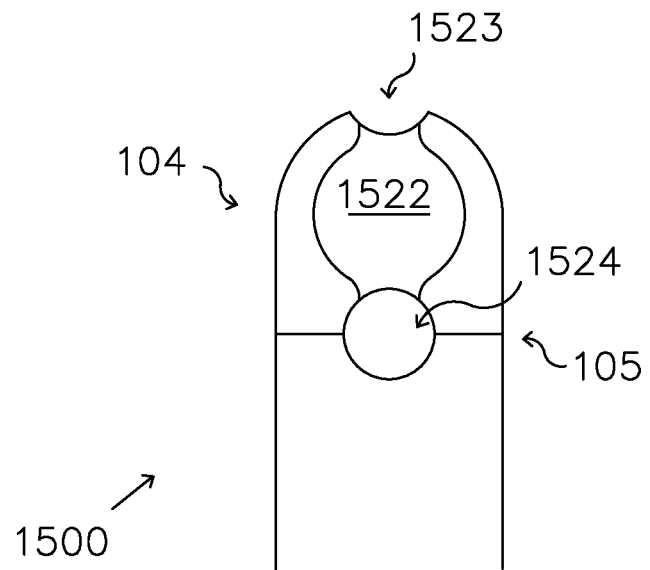

With reference to FIG. 15B, the sample collecting portion 104 of the sample transfer device 1500 comprises a cavity 1522 of a substantially circular shape. The cavity 1522 is defined by two opposing and substantially parallel inner surfaces provided by a first outer layer 1531 (FIG. 15C) and a second outer layer 1532 (FIG. 15E) and a perforation 1570 through an inner spacer layer 1530 (FIG. 15D).

A perforation 1580 through the device thickness (FIGS. 15C-15E) provides for the aperture 1523 (FIG. 15B) to act as the inlet port of the cavity 1522 of the sample collecting portion. A perforation 1590 through the device thickness (FIGS. 15C-15E) provides for the reduction of the device resisting cross section at the frangible portion 105, thereby providing a weakened portion for controlled separation of the collecting and handling portions, and also provides for the aperture 1524 (FIG. 15B) to act as the air vent of the cavity 1522 of the sample collecting portion. By providing the air vent opening in the frangible portion, the device can be manufactured in less steps or with less cuts and a more compact arrangement of the sample collecting portion is enabled.

The use of single cuts through the device thickness to provide for both the inlet port and the air vent also prevents the liquid sample to be removed from the cavity 1522 through the inlet port 1523 or through the air vent 1524, when a tissue paper or other absorbing medium is used to clean the external surface of the sample transfer device 1500.

Figure 16:
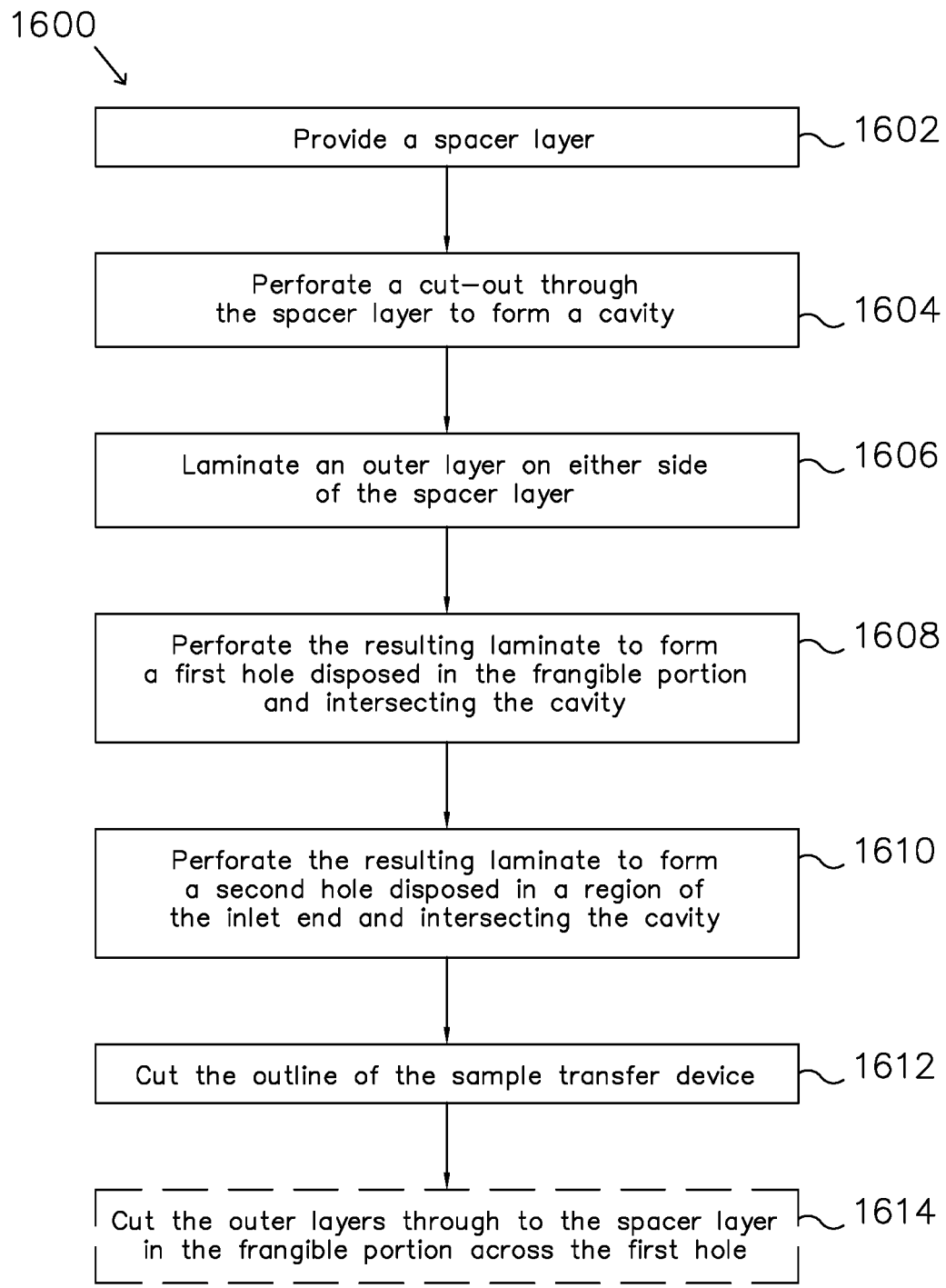
FIG. 16 illustrates a method of manufacturing a sample transfer device.

With reference to FIG. 16, a method of manufacturing a sample transfer device, for example as described above, comprises providing 1602 a spacer layer (comprising a single layer of material, laminate comprising a spacer material with an intermediate layer laminated to it one or both sides, or a laminate of any suitable number of layers), for example inner spacer layer 1530, and perforating 1604 a cut-out through the spacer layer to form a cavity, for example perforation 1570. The perforated spacer layer is then laminated 1606 on either side with a coven outer layer, for example outer layers 1531 and 1532, in some embodiments with a hydrophilic surface of the outer layers facing the spacer layer. The resulting laminate is then perforated 1608 to form a first hole intersecting the cavity to provide the reduced cross-section of the frangible portion and the air vent, for example perforation 1590. The laminate is further perforated 1610 to form a second hole intersecting the cavity and disposed in a region of an inlet end of the sample transfer device to provide the inlet opening and perforated 1612 to cut out the outline of the sample transfer device (individually or as part of a connected set of sample transfer devices), with the intersection between the perforations and steps 1610 and 1612 forming a notch at the inlet end. Where desired, the outer layers may be cut 1614 through to the spacer layer, cutting any intermediate layers down to the spacer layer material if needed, in the frangible portion across the first hole. This may be useful to facilitate a clean break in the frangible portion, for example when the outer layer materials are malleable rather than brittle. It will be appreciated that steps 1608 to 1614 can be performed in any order and can be grouped to be performed simultaneously as convenient based on the design of the relevant cutting tools.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described but can be practiced with modifications and alterations within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

For one example, embodiments of the sample transfer device comprising multiples cavities for collection of individual sample volumes can be configured in many different ways. Additionally, embodiments providing multiple apertures (i.e. multiple inlet ports) per cavity could be used, for example, to divide the volume of the liquid sample in multiple fractions when transferring the sample from the sample transfer device to a second device. These are considered within the spirit and scope of the present disclosure.

The invention claimed is:

1. A sample transfer device comprising a sample collecting portion and a handling portion separated by a frangible portion, wherein the sample collecting portion comprises a cavity having a first opening at an inlet end of the sample transfer device to allow a sample liquid to be drawn into the cavity and a second opening to allow air to escape from the cavity as liquid is drawn into the cavity and wherein the frangible portion comprises a weak section of material with reduced resistance to breaking compared to adjacent sections of the sample transfer device adjacent to the weak section to facilitate separation of the sample collecting portion and the handling portion.

2. The sample transfer device according to claim 1, wherein the cavity has at least one surface presenting a hydrophilic material to the inside of the cavity.

3. The sample transfer device according to claim 1, wherein the cavity is defined by a through-hole in a spacer layer sandwiched between a respective outer layer on each side of the spacer layer, each outer layer forming a wall of the cavity.

4. The sample transfer device according to claim 3, wherein the spacer layer comprises a material exhibiting brittle fracture upon folding or shearing.

5. The sample transfer device according to claim 3, wherein the spacer layer comprises a material selected from the group of: Poly(methyl methacrylate), Polystyrene, Polylactic Acid, Polyvinyl Chloride, Polycarbonate, Styrene-acrylonitrile, Cyclic Olefin Copolymer.

6. The sample transfer device according to claim 3, wherein the spacer layer comprises Poly(methyl methacrylate).

7. The sample transfer device according to claim 3, wherein the spacer layer comprises a material capable of being provided as a roll for roll to roll processing.

8. The sample transfer device according to claim 3, wherein the first opening is provided by a notch in the inlet end of the sample transfer device extending through the spacer and outer layers.

9. The sample transfer device according to claim 3, wherein the second opening is provided by a hole extending through the spacer layer and outer layers.

10. The sample transfer device according to claim 9, wherein the hole is in the frangible portion to provide the weak section of material.

11. The sample transfer device according to claim 8, wherein the notch and/or hole have a rounded contour.

12. The sample transfer device according to claim 9, wherein the hole is substantially circular.

13. The sample transfer device according to claim 3, wherein the outer layers are cut across the frangible portion through to the spacer layer to provide the weak section of material.

14. The sample transfer device according to claim 3, wherein the at least one of the outer layers comprises a hydrophilic side facing the spacer layer.

15. The sample transfer device according to claim 14, wherein the spacer layer is sandwiched between an intermediate layer on each side and the laminate of the spacer and intermediate layers is sandwiched on each side between the outer layers, the cavity being formed by a through-hole through the intermediate and spacer layers.

16. The sample transfer device according to claim 1, wherein the sample transfer device is translucent or transparent in a first region coinciding with the cavity and opaque in a second region surrounding the first region.

17. The sample transfer device according to claim 16, wherein the sample transfer device is white in the second region.

18. The sample transfer device according to claim 15, wherein one or both of the intermediate layers are opaque.

19. The sample transfer device according to claim 18, wherein one or both of the intermediate layers are white.

20. The sample transfer device as claimed in claim 1, wherein an absorbent material is disposed inside the cavity.

21. The sample transfer device as claimed in claim 1, wherein the cavity has a substantially circular shape.

22. A kit comprising the sample transfer device as claimed in claim 1 and a microfluidic liquid sample processing device, wherein the microfluidic liquid sample processing device comprises an opening in an outer surface of the processing device giving access to the sample collecting portion to a space inside the processing device, wherein the opening comprises an edge and the space is dimensioned to accommodate the sample collecting portion with the frangible portion resting against or adjacent the edge when the sample collecting portion is fully inserted into the space.

23. A kit according to claim 22, wherein the liquid sample processing device comprises a centrifugal microfluidic liquid sample processing device having a body to be rotated about an axis of rotation to drive liquid flows inside the device, the device comprising an inlet port in a planar surface of the body intersecting the axis of rotation for receiving a sample transfer device, wherein the inlet port comprises an opening in the planar surface of the device giving access to the sample transfer device to an undercut below the planar surface defining an internal cavity to accommodate and hold in place a portion of the sample transfer device in an orientation substantially parallel to the planar surface and wherein the opening defines an edge for engagement with a portion of the sample transfer device.

24. A method of manufacturing a device as claimed in claim 3, the method comprising cutting through the spacer layer to form the cavity, making a first cut through the spacer layer and outer layers to form the first opening and making a second cut through the spacer layer and outer layers to form the second opening and frangible portion.

* * * * *